US008386273B2

(12) United States Patent
Kaminaga et al.

(10) Patent No.: US 8,386,273 B2
(45) Date of Patent: Feb. 26, 2013

(54) MEDICAL IMAGE DIAGNOSTIC APPARATUS, PICTURE ARCHIVING COMMUNICATION SYSTEM SERVER, IMAGE REFERENCE APPARATUS, AND MEDICAL IMAGE DIAGNOSTIC SYSTEM

(75) Inventors: Shigeo Kaminaga, Otawara (JP); Masahiro Ozaki, Otawara (JP); Takashi Masuzawa, Otawara (JP); Akira Iwasa, Nasushiobara (JP); Hitoshi Kanazawa, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 656 days.

(21) Appl. No.: 11/697,930

(22) Filed: Apr. 9, 2007

(65) Prior Publication Data
US 2007/0238963 A1 Oct. 11, 2007

Related U.S. Application Data

(63) Continuation of application No. PCT/JP2006/323618, filed on Nov. 27, 2006.

(30) Foreign Application Priority Data

Nov. 25, 2005 (JP) ................................ 2005-341087

(51) Int. Cl.
*G06Q 10/00* (2006.01)
(52) U.S. Cl. ........................................................ 705/2
(58) Field of Classification Search ....... 378/4; 600/407, 600/410, 425, 426–429; 382/128; 705/2
See application file for complete search history.

(56) References Cited

U.S. PATENT DOCUMENTS

| 6,195,409 | B1 | 2/2001 | Chang et al. |
| 7,116,807 | B1 | 10/2006 | Brackett |
| 2002/0016718 | A1* | 2/2002 | Rothschild et al. ............... 705/2 |
| 2003/0144589 | A1 | 7/2003 | Roell |
| 2004/0076257 | A1 | 4/2004 | McDaniel et al. |
| 2005/0154292 | A1 | 7/2005 | Tank |

FOREIGN PATENT DOCUMENTS

| CN | 1654009 A | 8/2005 |
| EP | 315 155 A2 | 5/2003 |
| EP | 315 155 A3 | 5/2003 |
| JP | 5-81353 A | 4/1993 |
| JP | 6-90938 | 4/1994 |
| JP | 9-81646 | 3/1997 |
| JP | 2000-152928 A | 6/2000 |
| JP | 2002-253552 A | 9/2002 |
| JP | 2003-141250 | 5/2003 |

(Continued)

OTHER PUBLICATIONS

U.S. Appl. No. 12/100,736, filed Apr. 10, 2008, Matsue, et al.

(Continued)

*Primary Examiner* — Elmer Chao
(74) *Attorney, Agent, or Firm* — Oblon, Spivak, McClelland, Maier & Neustadt, L.L.P.

(57) ABSTRACT

A shared object is newly created in a unified format with respect to past medical information that is effective in a photographing step or a report creating step. Since the shared object can include a position determination image, unique object information, body coordinates information, a photographing condition, a image creating condition, and key image information, it is possible to automatically set the same photographing condition, photographing range, a tomographic position to be photographed, and image creating condition as those in a past test by using the information described above.

11 Claims, 27 Drawing Sheets

FOREIGN PATENT DOCUMENTS

| | | |
|---|---|---|
| JP | 2003-164442 | 6/2003 |
| JP | 2003-275199 | 9/2003 |
| JP | 2004-305289 A | 11/2004 |
| JP | 2005-27978 A | 2/2005 |
| JP | 2005-118257 | 5/2005 |
| JP | 2005-296436 A | 10/2005 |
| JP | 2005-327302 A | 11/2005 |
| WO | WO 02/43003 A1 | 5/2002 |
| WO | WO 2005/088328 A2 | 9/2005 |
| WO | WO 2005/088328 A3 | 9/2005 |

OTHER PUBLICATIONS

U.S. Appl. No. 12/246,117, filed Oct. 6, 2008, Yamagishi, et al.
U.S. Appl. No. 12/260,395, filed Oct. 29, 2008, Futami, et al.
Office Action issued Apr. 24, 2012 in Japanese Application No. 2006-319356 (With English Translation).
Japanese Office Action Issued Aug. 21, 2012 in Patent Application No. 2006-319356 (with English translation).

* cited by examiner

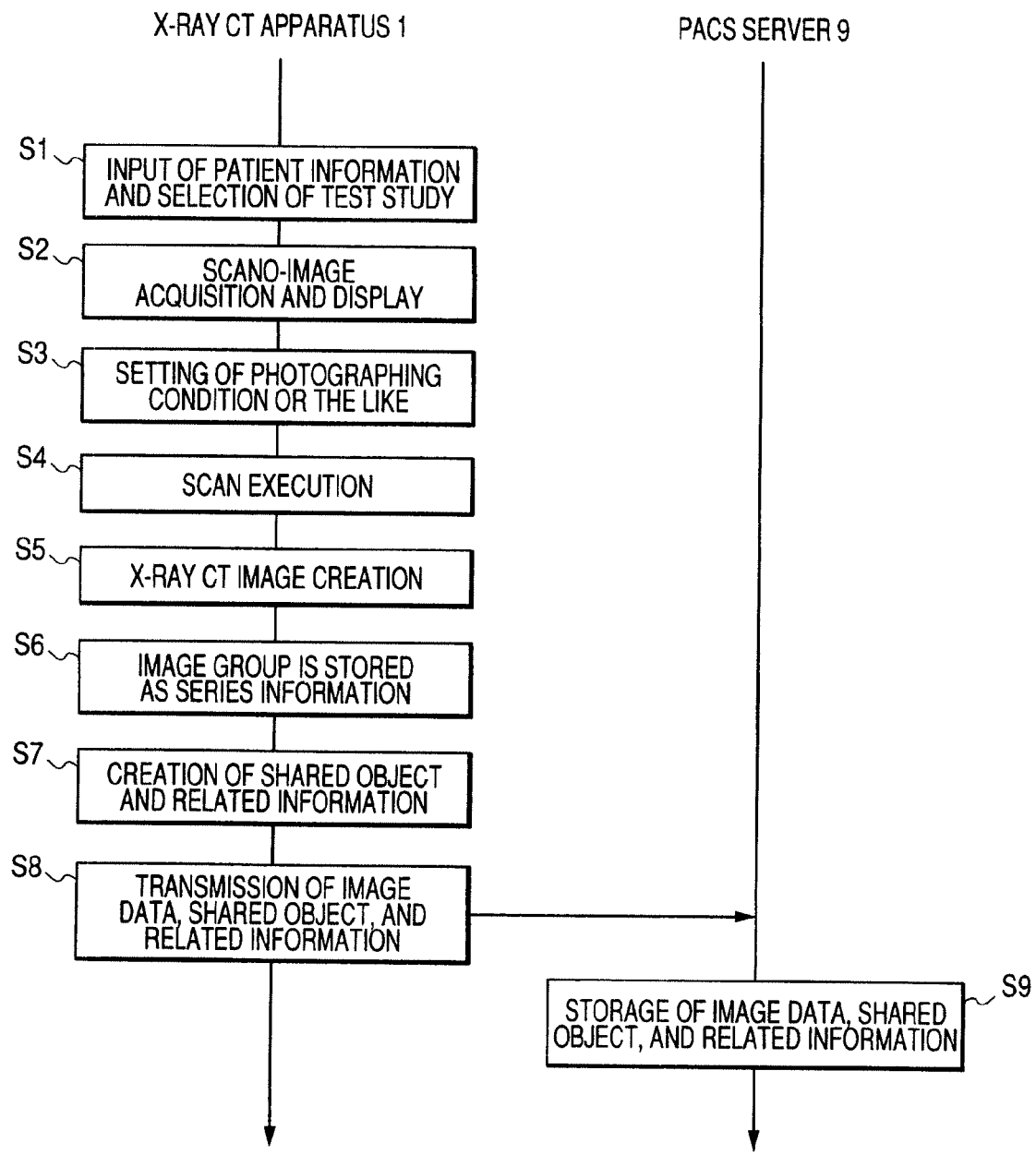

FIG. 25

DIAGNOSTIC PROTOCOL

| SERIES NUMBER | PHOTOGRAPHED PART | IMAGE CREATION CONDITION |
|---|---|---|
| SERIES 1-1 | CHEST | SAGITTAL IMAGE··· |
| SERIES 1-2 | CHEST | AXIAL IMAGE··· |
| ··· | ··· | ··· |
| ··· | ··· | ··· |
| SERIES 1-n | CHEST | ··· |
| SERIES 2-1 | ABDMEN | SAGITTAL IMAGE··· |
| SERIES 2-2 | ABDMEN | AXIAL IMAGE··· |
| ··· | ··· | ··· |
| SERIES 2-m | ABDMEN | AXIAL IMAGE |

MEDICAL IMAGE DIAGNOSTIC APPARATUS, PICTURE ARCHIVING COMMUNICATION SYSTEM SERVER, IMAGE REFERENCE APPARATUS, AND MEDICAL IMAGE DIAGNOSTIC SYSTEM

CROSS REFERENCE TO RELATED APPLICATIONS

This is a Continuation Application of PCT Application No. PCT/JP2006/323618, filed Nov. 27, 2006, which was published under PCT Article 21(2) in Japanese.

This application is based upon and claims the benefit of priority from prior Japanese Patent Application No. 2005-341087, filed Nov. 25, 2005, the entire contents of which are incorporated herein by reference.

BACKGROUND OF THE INVENTION

1. Field of the Invention

The present invention relates to a medical image diagnostic apparatus that creates an image from data obtained by scanning a tested body placed on a bed, a picture archiving communication system server (PACS server) connected to a medical image diagnostic apparatus, an image reference apparatus for observing an image acquired by a medical image diagnostic apparatus, and a medical image diagnostic system having the medical image diagnostic apparatus, the picture archiving communication system server, and the image reference apparatus.

2. Description of the Related Art

In recent years, areas of expertise of medical act are divided into parts. For example, an image diagnosis is divided into works including acquisition of a diagnostic image of a patient, reading of the acquired diagnostic image and report creation, and explanation of a diagnostic result or a treatment course based on the report result. Each expert (doctor in charge or technician in charge) is in charge of each of the works, and the medical act, such as diagnosis of a patient, is accomplished by collaborate works of the experts. Each of the experts performs each work on the basis of information, which is created by the other experts in a work of a previous step, and by properly referring past diagnostic information. These works are performed by using a medical image diagnostic apparatus, such as an X-ray CT apparatus or an MRI apparatus, which acquires a diagnostic image, a PACS server that stores diagnostic images, or an image reference apparatus for reading a diagnostic image, for example.

FIG. 29 is a view illustrating an example of a flow (from request from a patient to image test) of a medical act in an image diagnosis. As shown in the drawing, first, a requested doctor (family doctor) makes a test (study) order on the basis of a medical interview with a patient and sends the test order to a test technician (step Sa). Here, the order is transmitted to a variety of medical image diagnostic apparatuses through a network or the like by using an order system and refers to a request for a next test to be done.

Then, a test technician executes a test by the use of a predetermined medical image diagnostic apparatus so as to acquire an image of an affected part (step Sb). This test is executed by selecting a desired test from a list of test request (based on the test order) displayed on a monitor of a medical image diagnostic apparatus, for example. Thus, the test is executed on the basis of a principle test order. However, information described above may not be sufficient to determine a test method, a range/direction to be photographed, and a photographing condition. In this case, the test technician executes the test by referring to a previous test image, a previous report, and a key image (image serving as a basis of diagnosis) related to the previous report, in consideration of the range/direction of photographing and the photographing condition so that an image corresponding to the previous image can be obtained. Acquired image data is output from the medical image diagnostic apparatus as digital data and is stored in a PACS server, for example. Moreover, in the medical image diagnostic apparatus and the PACS server, an image is generally managed under a state where there are divided layers corresponding to study, series (indicator for distinguishing a one-time scan process), and an image. Accordingly, when the scan process is performed several times in a test, a plurality of series information corresponding to the test is stored and a plurality of images corresponding to the series (that is, the scan process thereof) is stored in each series.

Then, a doctor, who reads an image, in a department of radiology creates an image-reading report corresponding to the test order (step Sc). At this time, it is important to make a diagnose while comparing an image serving as a basis of a previous image diagnosis, that is, a key image related to a previous report with a present test image. Thus, the doctor, who reads an image, in a department of radiology checks details of request by referring to the order, checks points to be read by referring to the previous test report or image, and reads an image of a present test (performs an image diagnosis).

Then, a requesting doctor determines a result of the image diagnosis by referring to the created report (step Sd). That is, the requesting doctor analyzes details of the report while referring to the key image (image serving as a basis of diagnosis) related to the report and performs the diagnosis on the basis of the report and other information not shown, thus performing medical treatment.

However, a known medical image diagnostic system has the following problems.

In performing a comparative diagnosis referring to a past test, it is desired that details of a present test be close to details of the past test. However, in a known system, the test technician makes a test plan by referring to a past test image or film image stored in a file server or referring to information added in an image of the past test. However, the past test image or film image is basically used for image reading but is not used for a reference of a test (photographing). Accordingly, there occurs a problem that information required for the present test cannot be acquired, there is an item set by imagination based on a past image or the like, or a photographing condition where the same setting as previous setting cannot be made occurs. In particular, in a cross-sectional image such as an MRI image or an X-ray CT image, it is difficult for a test technician to figure out information on a photographing position, a reconstruction range, or the like.

Furthermore, in general, the position and posture of a patient on a top board of a bed are different from those previously set, in many cases, due to conditions (of both a patient and an operator) at the time of setting. Accordingly, precision for the comparative diagnosis may not be sufficiently obtained only by using a photographing plan (for example, a scan range and a reconstruction position) of the previous test.

BRIEF SUMMARY OF THE INVENTION

The present invention is designed in consideration of the above situation, and it is an object of the present invention to provide a medical image diagnostic apparatus, a picture archiving communication system server, an image reference apparatus, and a medical image diagnostic system that are capable of creating shared information, by which medical information in the past can be widely applied and be reproduced with high precision, and of efficiently utilizing the shared information.

According to a first aspect of the invention, a medical image diagnostic apparatus includes: an input unit for inputting scan position information by using a scan condition and an image for position determination of a tested body; a data acquisition unit that acquires data for creating an image on the basis of the scan condition and the scan position information; an image creating unit that creates an image on the basis of the data for creating the image; a storage unit that stores the image; and an object creating unit that creates an object in which the scan condition and the scan position information are added in the position determination image.

According to a second aspect of the invention, an image reference apparatus includes: a storage unit that stores a group of images acquired in a predetermined image acquisition process; an operation unit for selecting a first image from the acquired image group and inputting an image processing condition for creating a second image on the basis of the selected first image; an image creation processing unit that creates the second image by performing image processing using the first image according to the image processing condition; and an object creating unit that creates an object in which the image processing condition is added in the first image.

According to a third aspect of the invention, an image reference apparatus includes: a storage unit that stores a first object including, as information for indicating characteristics related to an image creating process for creating a first diagnostic image on the basis of a first image selected from a plurality of images acquired in a first image acquisition process, information for specifying the first image acquisition process, information for selecting the first image, and a first image creating condition used in the image creating process; a control unit that selects a second image from a plurality of images used in a second image acquisition process on the basis of the information for selecting the first image and sets a second image creating condition used in an image creating process, in which a second diagnostic image is created on the basis of the second image, on the basis of the first image creating condition; and an image creation processing unit that creates the second diagnostic image according to the set second image creating condition.

According to a fourth aspect of the invention, a picture archiving communication system server includes: a storage unit that stores a plurality of images acquired in a predetermined image acquisition process, each of the plurality of images being added with accessory information on a condition used in the corresponding image acquisition process or a condition used in an image creating process thereafter; and an object creating unit that creates an object which is information for indicating a characteristic of the predetermined image acquisition process or the image creating process thereafter on the basis of the accessory information of each of the images.

According to a fifth aspect of the invention, a medical image diagnostic system includes: a medical image diagnostic apparatus connected to a network; and a picture archiving communication system server connected to the network. The medical image diagnostic apparatus includes: an input unit for inputting an image creating condition and a photographing condition including a photographing range with respect to a position determination image of a tested body; a data acquisition unit that acquires imaging data for imaging the photographing range of the tested body on the basis of the photographing condition; an image creating unit that creates a plurality of images by executing image reconstruction using the imaging data according to the image creating condition; a storage unit that stores the plurality of images; and an object creating unit that creates an object including at least the photographing condition, the image creating condition, and the position determination image, the object being information for indicating a characteristic related to a process of acquiring the plurality of images. The picture archiving communication system server includes: a receiving unit that receives the object and the related information from the medical image diagnostic apparatus through the network; and a storage unit that stores the received object and the received related information.

According to a sixth aspect of the invention, a medical image diagnostic system includes: a medical image diagnostic apparatus connected to a network; and a picture archiving communication system server connected to the network. The picture archiving communication system server includes: a storage unit that stores a first object including, as information for indicating characteristics related to a predetermined image acquisition process in the past, at least information on a first position determination image used in the image acquisition process, a first photographing condition used in the image acquisition process, and a position of a first photographing range set by using the first position determination image in the image acquisition process; and a transmitting unit that transmits the first object to the medical image diagnostic apparatus through the network in response to a request. The medical image diagnostic apparatus includes: a receiving unit that receives the first object from the transmitting unit through the network; an object analysis unit that performs spatial coordination between the first position determination image and a second position determination image used in a present image acquisition process on the basis of the received first object; a control unit that sets a second photographing condition used in the present image acquisition process on the basis of the first photographing condition; and a display unit that displays the first position determination image in which the first photographing range is set and the second position determination image such that the first position determination image and the second position determination image spatially coordinate with each other.

According to a seventh aspect of the invention, a medical image diagnostic system includes: an image reference apparatus connected to a network; and a picture archiving communication system server connected to the network. The image reference apparatus includes: an acquisition unit that acquires a group of images, which is acquired in a predetermined image acquisition process, from the picture archiving communication system server through the network; an operation unit for selecting a first image from the acquired image group and inputting an image creating condition which is a condition of image processing on the selected first image; an image creation processing unit that creates a second image by performing image processing using the first image according to the image creating condition; and an object creating unit that creates an object including at least the image creating condition and information for specifying the predetermined image acquisition process, the object being information for indicating a characteristic of the image creating condition. The picture archiving communication system server includes: a receiving unit that receives the object and the related information from the medical image diagnostic apparatus through the network; and a storage unit that stores the received object and the received related information.

According to an eighth aspect of the invention, a medical image diagnostic system includes: an image reference apparatus connected to a network; and a picture archiving communication system server connected to the network. The picture archiving communication system server includes: a storage unit that stores a first object including, as information for indicating characteristics related to an image creating process for creating a first diagnostic image on the basis of a first image selected from a plurality of images acquired in a first image acquisition process, information for specifying the first image acquisition process, information for selecting the first image, and a first image creating condition used in the image creating process; and a transmitting unit that transmits the first object to the medical image diagnostic apparatus through the network in response to a request. The image reference apparatus includes: a control unit that selects a second image from a plurality of images used in a second image acquisition process on the basis of the information for selecting the first image and sets a second image creating condition used in an image creating process, in which a second diagnostic image is created on the basis of the second image, on the basis of the first image creating condition; and an image creation processing unit that creates a diagnostic image by executing image processing according to the set image creating condition.

BRIEF DESCRIPTION OF THE SEVERAL VIEWS OF THE DRAWING

FIG. 7 is a timing chart illustrating a flow of a process performed by the X-ray CT apparatus 1 in creating a shared object;

FIG. 25 is a series selection screen displayed when a shared object created in a test using an X-ray CT apparatus is used in an MRI apparatus;

DETAILED DESCRIPTION OF THE INVENTION

Figure 1:
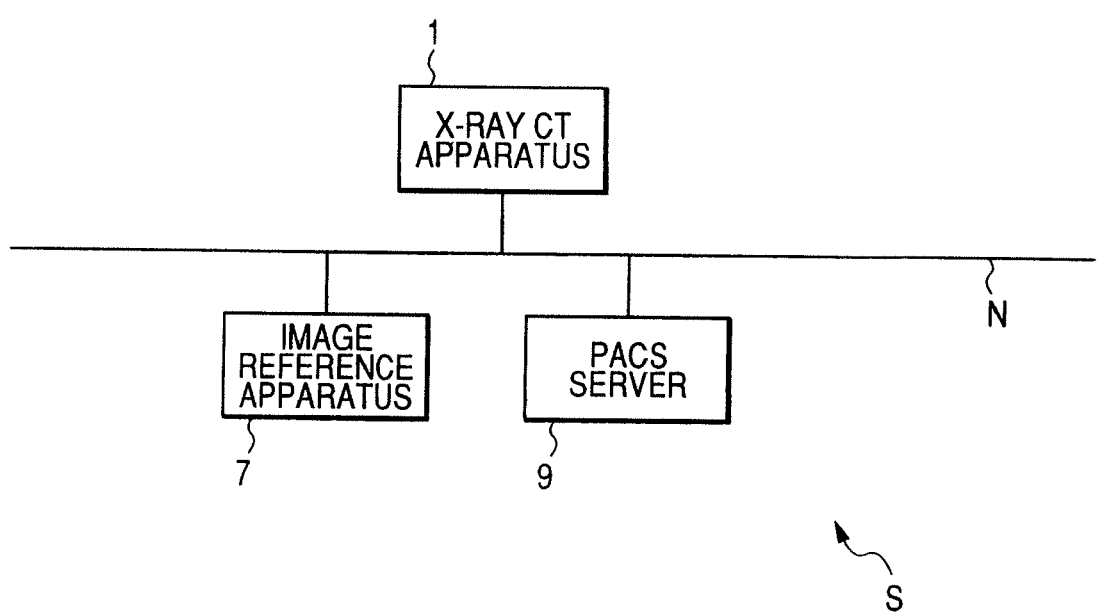
FIG. 1 is a view illustrating the configuration of a medical image diagnostic system S according to a first embodiment.

Hereinafter, first to fifth embodiments of the present invention will be described with reference to accompanying drawings. In the following description, constituent members having approximately the same functions and configurations have the same reference numerals, and a repeated explanation will be made as necessary.

First Embodiment (Medical Image Diagnostic System)

FIG. 1 is a view illustrating the configuration of a medical image diagnostic system S according to the present embodiment. As shown in the drawing, the medical image diagnostic system S is build by using a hospital information system (HIS) and includes a medical image diagnostic apparatus (X-ray computerized tomography apparatus 1; hereinafter, referred to as an 'X-ray CT apparatus 1'), an image reference apparatus 7, and a PACS server 9, which are all connected to a network N.

In addition, in FIG. 1, an example is shown in which the X-ray CT apparatus 1 is used as a medical image diagnostic apparatus. However, the technical scope of the present invention is not limited thereto. For example, the present invention may be applied to other apparatuses that determine the photographing position by the use of a bed, such as a magnetic resonance imaging apparatus (MRI apparatus), an X-ray diagnostic apparatus, or a nuclear medicine diagnostic apparatus. Furthermore, in FIG. 1, there is shown an example of the medical image diagnostic system S built by using an information system within a hospital. However, a medical image diagnostic system may be configured to include a medical image diagnostic apparatus, a PACS server, an image reference apparatus, and a medical terminal provided in other medical institutes or research institutes, through Internet without being limited to the example described above.

(X-Ray CT Apparatus)

The X-ray CT apparatus 1 performs scan sequences for acquiring X-ray projection data, creation of an X-ray tomographic image based on image reconstruction using the X-ray projection data, a display play, and the like. In addition, the X-ray CT apparatus 1 or the like performs a process of creating a shared object by using conditions used in image processing, such as a scan process, the reconstruction of the X-ray CT image, volume rendering, or an MPR process.

Figure 2:
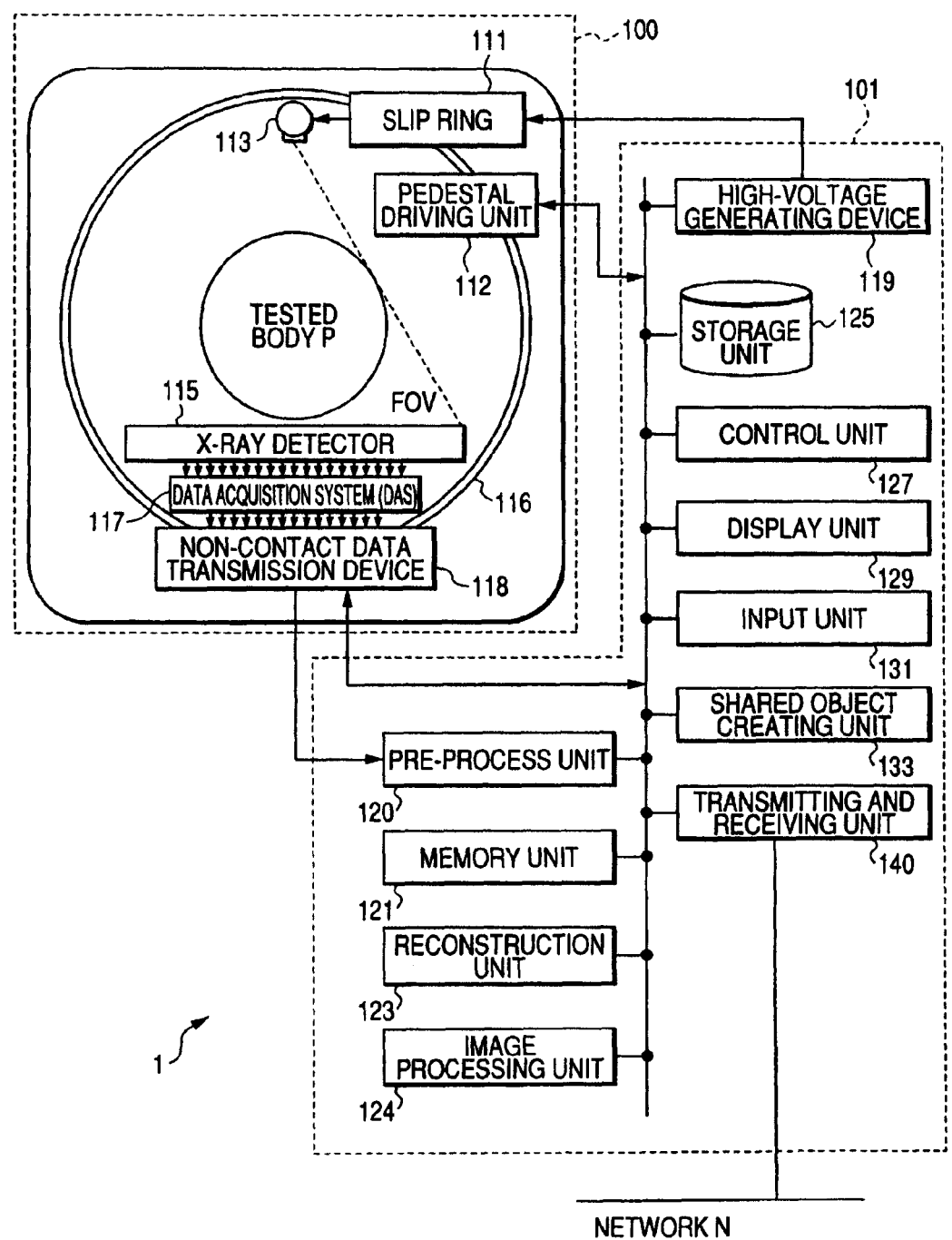
FIG. 2 is a block diagram illustrating the configuration of an X-ray CT apparatus 1 according to the first embodiment.

FIG. 2 is a block diagram illustrating the configuration of the X-ray CT apparatus 1. As shown in FIG. the X-ray CT apparatus 1 includes a pedestal 100 and an information process part 101. The pedestal 100 is configured to acquire projection data on a tested body P and includes a slip ring 111, a pedestal driving unit 112, an X-ray tube 113, an X-ray detector 115, a rotary frame 116, a data acquisition system 117, and a non-contact data transmission apparatus 118. The information process part 101 controls a data acquisition operation in the pedestal 100 and performs a predetermined process on data acquired in the pedestal 100 so as to create an X-ray CT image and a variety of clinical information using the same. The information process part 101 includes a high-voltage generating device 119, a pre-process unit 120, a memory unit 121, a reconstruction unit 123, an image processing unit 124, a storage unit 125, a control unit 127, a display unit 129, an input unit 131, a shared object creating unit 133, and a transmitting and receiving unit 140.

The pedestal driving unit 112 drives the rotary frame 116 such that the rotary frame 116 rotates. Due to the rotational driving, the X-ray tube 113 and the X-ray detector 115 spirally rotate around a body axis of the tested body P while the X-ray tube 113 is opposite to the X-ray detector 115.

The X-ray tube 113 is a vacuum tube that generates X rays and is provided in the rotary frame 116. Power (tube current, tube voltage) required for X-ray exposure is supplied from the high-voltage generating device 119 to the X-ray tube 113 through the slip ring 11. In the X-ray tube 113, electrons are accelerated by the supplied high voltage to collide with a target, such that X rays are exposed onto a tested body placed within an effective viewing region FOV.

The X-ray detector 115 is a detector system that detects X rays transmitted through the tested body and is mounted in the rotary frame 116 so as to be opposite to the X-ray tube 113. The X-ray detector 115 is a single-slice type detector or a multi-slice type detector. In the X-ray detector 115, a plurality of detection elements composed of a combination of scintillators and photodiodes are arranged in one-dimensional or two-dimensional manner according to the type of the X-ray detector 115.

The rotary frame 116 is a ring that is driven to rotate around a Z axis, and the X-ray tube 113 and the X-ray detector 115 are mounted therein. A central portion of the rotary frame 116 is open, and the tested body P placed in a bed (not shown) is inserted into the opening.

The data acquisition system 17 is generally called a DAS (data acquisition system), converts a signal, which is output from the detector 15 for each channel, to a voltage signal, amplifies the converted signal, and converts the amplified signal to a digital signal. The raw data is supplied to an information processing apparatus 3 through the movement amount operation circuit 18.

The high-voltage generating device 119 is a device that supplies power required for X-ray exposure to the X-ray tube 113 through the slip ring 11 and includes a high-voltage transformer, a filament heating and converting unit, a rectifier, a high-voltage switch, and the like.

The pre-process unit 120 receives the raw data from the data acquisition system 17 through the non-contact data transmission apparatus 18 so as to perform sensitivity correction or X-ray intensity correction. Raw data corresponding to a predetermined angular range, for which the variety of corrections has been made, is first stored in the storage unit 125. In addition, the raw data for which the pre-process has been performed by the pre-process unit 120 is called 'projection data'.

The reconstruction unit 123 uses a plurality of kinds of reconstruction methods and reconstructs image data according to an image creating condition set by a reconstruction method selected by an operator. The plurality of kinds of reconstruction methods include, for example, a fan beam reconstruction method (also referred to as a fan beam convolution/back projection method), a Feldkamp method which is a reconstruction method when projected rays obliquely intersect a reconstruction plane, and a cone beam reconstruction method. The Feldkamp method is an approximate image reconstruction method in which convolution processing is performed by regarding data as a fan projection beam and back projection processing is performed along a ray in a scan on the assumption that the cone angle is small. The cone beam reconstruction method is a method for suppressing cone angle errors as compared with the Feldkamp method. In the cone beam reconstruction method, projection data is corrected in accordance with the angle of a ray with respect to a reconstruction plane.

The image processing unit 124 performs image processing (post process), such as volume rendering and MPR process, with respect to reconstruction image data created by the reconstruction unit 123 and outputs it to the display unit 129.

The storage unit 125 stores image data, such as tomographic image data, raw data, projection data, or scanogram data, a program for a test plan. In addition, the storage unit 125 stores a dedicated program for realizing a shared object creating function or the like to be described later.

The control unit 127 performs an overall control of the X-ray CT apparatus 1 in a scan process, signal processing, an image creating process, an image display process, and the like. For example, in the scan process, according to set photographing (scan) conditions, the control unit 127 controls the high-voltage generating device 119, the pedestal driving unit 12, movement amount and movement speed of a top board of a bed in the body-axis direction, rotation speed and rotation pitch of the X-ray tube 113 and the X-ray detector 115, and exposure timing of an X ray, and the like, and exposes X-ray cone beams or X-ray fan beams on a desired photographing part of the tested body from multiple directions so as to perform a data acquisition (scan) process of an X-ray CT image. In addition, the control unit 127 loads a dedicated program stored in the storage unit 125 into a memory so as to realize a shared object creating function.

The display unit 129 is an output device that displays a dialog screen or the like for setting an X-ray CT image, a scanogram image, a photographing condition, an image creating condition, and the like input from the image processing unit 124. Moreover, in the present embodiment, an X-ray CT image is defined as an 'image created on the basis of each CT value within an FOV (photographing region) acquired by an X-ray computerized tomography apparatus'. Here, the CT value is a value obtained by expressing an X-ray absorption coefficient of a material as a relative value with respect to a reference material (for example, water). In addition, the display unit 129 displays a scan plan screen or the like realized by a plan aid system (not shown).

The input unit 131 includes a keyboard, a variety of switches, and a mouse and serves as a device through which an operator can input various scan conditions, such as a slice thickness or the number of slices.

The shared object creating unit 133 is realized by loading a dedicated program stored in the storage unit 125 into a memory within the control unit 127 and creates a shared object including a photographing condition, a position determination image (reference image), or the like used in scanning for X-ray projection data acquisition. For example, in the case of an X-ray CT apparatus, the reference image is a scout image acquired by moving a top board under a state in which an X-ray tube and a detector are fixed, and in the case of an MRI apparatus, the reference image is a coronal image. In addition, the shared object creating unit 133 creates a shared object including an image creating condition or the like used when reconstructing an image on the basis of projection data acquired by scan. A process of these shared objects will be described in detail later.

The transmitting and receiving unit 140 transmits/receives image data, patient information, and the like to/from other apparatuses through the network N. In particular, the transmitting and receiving unit 140 receives information (for example, patient information or a diagnostic part) on the photographing of corresponding tested body from an RIS (radiology information system) connected to the network N.

[Image Reference Apparatus]

The image reference apparatus 7 is used, for example, when a doctor creates a report or the like while reading an image, and the image reference apparatus 7 displays an image read from the PACS server 9 or performs predetermined image processing to create a diagnostic image and then displays the diagnostic image. In addition, the image reference apparatus 7 performs a process of creating a shared object, for example, in the post process of creating a diagnostic image.

Figure 3:
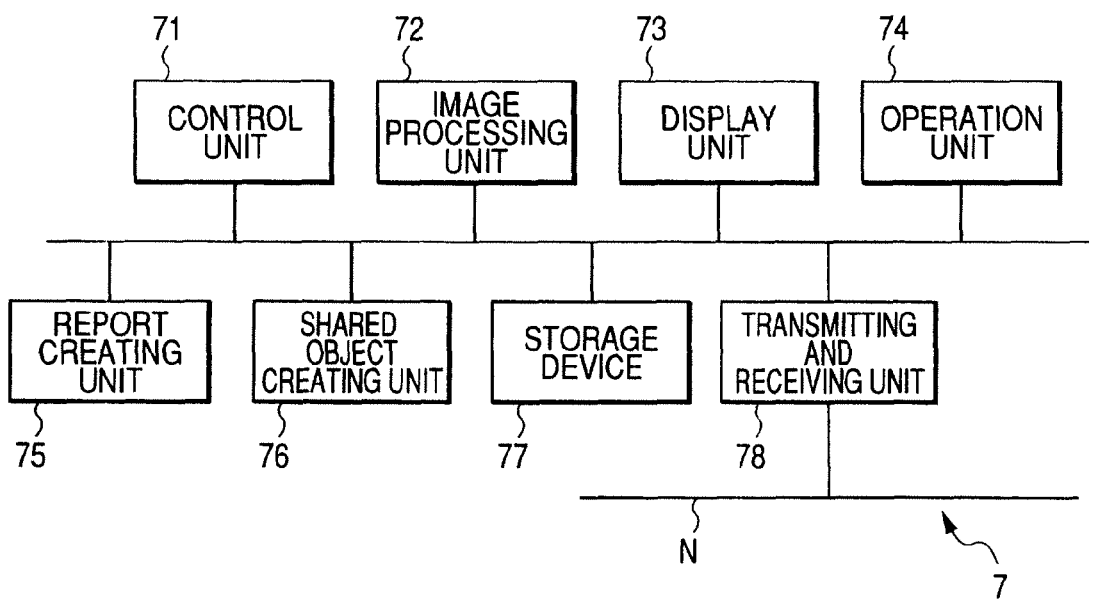
FIG. 3 is a block diagram explaining the configuration of an image reference apparatus 7 according to the first embodiment.

FIG. 3 is a block diagram explaining the configuration of the image reference apparatus 7. As shown in the drawing, the image reference apparatus 7 includes a control unit 71, an image processing unit 72, a display unit 73, an operation unit 74, a shared object creating unit 76, a storage device 77, and a transmitting and receiving unit 78.

The control unit 71 performs an overall control on a static or dynamic operation of the image reference apparatus 7. In addition, the control unit 71 loads a dedicated program stored in the storage device 77 into a memory (not shown), thereby realizing a shared object creating function.

The image processing unit 72 performs image processing, such as volume rendering and MPR process, by the use of image data acquired by a variety of medical image diagnostic apparatuses.

The display unit 73 displays a dialog screen or the like in a predetermined form, the dialog screen being used to set images acquired by a variety of medical image diagnostic apparatuses, images created by image processing in the image processing unit 72, or an image creating condition.

The operation unit 74 includes a keyboard, a variety of switches, and a mouse and serves as a device through which an instruction from an operator can be input.

The report creating unit 75 creates a report on the basis of an input from the operation unit 74.

The shared object creating unit 76 creates a shared object including a photographing condition, a position determination image, or the like used in scanning for X-ray projection data acquisition. In addition, the shared object creating unit 76 creates a shared object including an image creating condition, which is used for image reconstruction, and an image creating condition used in the post process, such as volume rendering or MPR process, on the basis of projection data acquired by scan.

The storage device 77 stores image data (including image data directly acquired from an apparatus and image data acquired from the PACS server 9) acquired by various medical image diagnostic apparatuses. In addition, the storage device 77 stores a dedicated program for realizing a shared object creating function or the like.

The transmitting and receiving unit 78 transmits/receives image data, patient information, and the like to/from other apparatuses through the network N. In particular, the transmitting and receiving unit 78 transmits the created shared object to the PACS server 9 through the network N.

[PACS Server]

The PACS server 9 manages and stores images created by various medical image diagnostic apparatuses and images created by post processes in the image reference apparatus 7 on the basis of a patient ID or the like. In addition, the PACS server 9 creates a shared object by using accessory information added to a past image, a position determination image related to past series, and the like.

Figure 4:
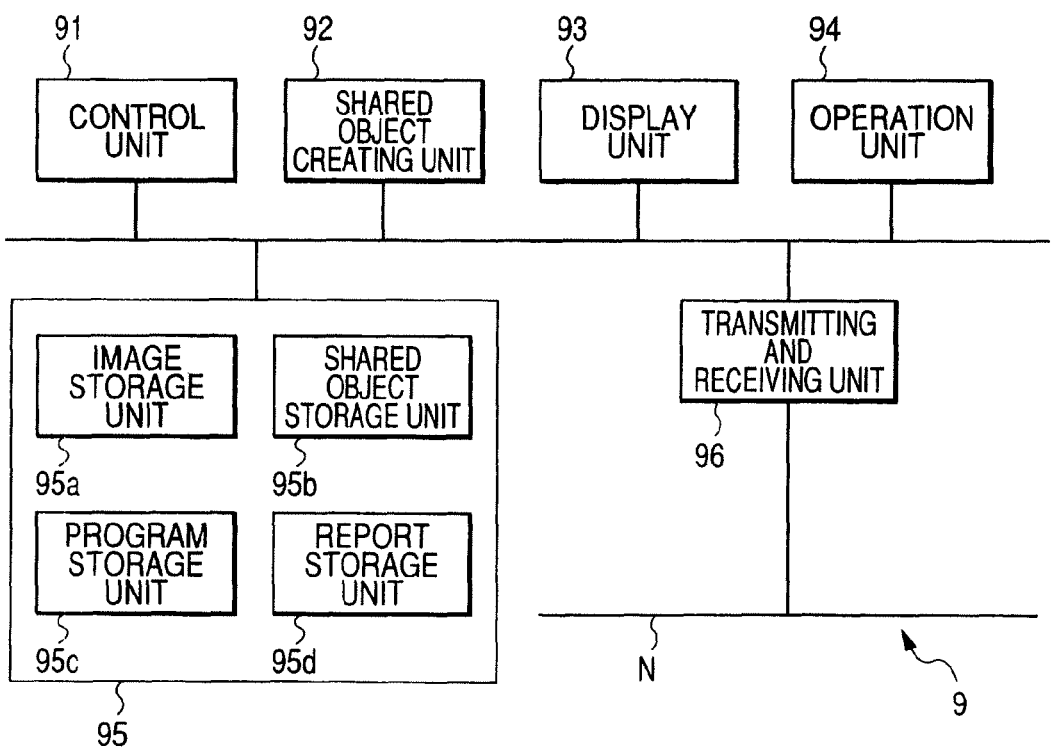
FIG. 4 is a block diagram explaining the configuration of a PACS server 9 according to the first embodiment.

FIG. 4 is a block diagram explaining the configuration of the PACS server 9. As shown in the drawing, the PACS server 9 includes a control unit 91, a shared object creating unit 92, a display unit 93, an operation unit 94, a storage device 95, and a transmitting and receiving unit 96.

The control unit 91 performs an overall control on a static or dynamic operation of the PACS server 9. In addition, the control unit 91 loads a dedicated program stored in the storage device 95 into a memory (not shown), thereby realizing a shared object creating function. In addition, the control unit 91 responds to a request from a medical image diagnostic apparatus or an image reference apparatus, searches corresponding image data and the shared object from the storage device 95, and transmits the searched image data and shared object through the network.

The shared object creating unit 92 performs a process of creating a shared object at a predetermined timing on the basis of accessory information added to a past image stored therein, a position determination image corresponding to each series, and the like.

The display unit 93 is a monitor on which an operation screen or a predetermined image is displayed.

The operation unit 94 includes a keyboard, a variety of switches, and a mouse and serves as a device through which an instruction from an operator can be input.

The storage device 95 includes an image storage unit 95a, a shared object storage unit 95b, a program storage unit 95c, and a report storage unit 95d. The image storage unit 95a stores images acquired by various medical image diagnostic apparatuses, order information used in a variety of tests, and the like. The shared object storage unit 95b stores a shared object created by the X-ray CT apparatus 1, the image reference apparatus 7, or itself. The program storage unit 95*c* stores a dedicated program for realizing a shared object creating function or the like. The report storage unit 95*d* stores information on a report created by a doctor who has read the image.

The transmitting and receiving unit 96 transmits/receives medical information, such as a shared object, to/from other apparatuses through the network N.

(Shared Object Creating Function)

Next, a shared object creating function that the X-ray CT apparatus 1, the PACS server 9, and the image reference apparatus 7 has will be described.

Here, the shared object creating function refers to a function of creating a shared object having image information and accessory (text or numeric values) in order to effectively use information (for example, a position determination image, a photographing position, a photograph range, a photographing condition, or an image creating condition) used when performing a medical act in the past. The shared object is created as information entity (for example, a file) that is separate from typical image data so as to be stored and managed.

Figure 5:
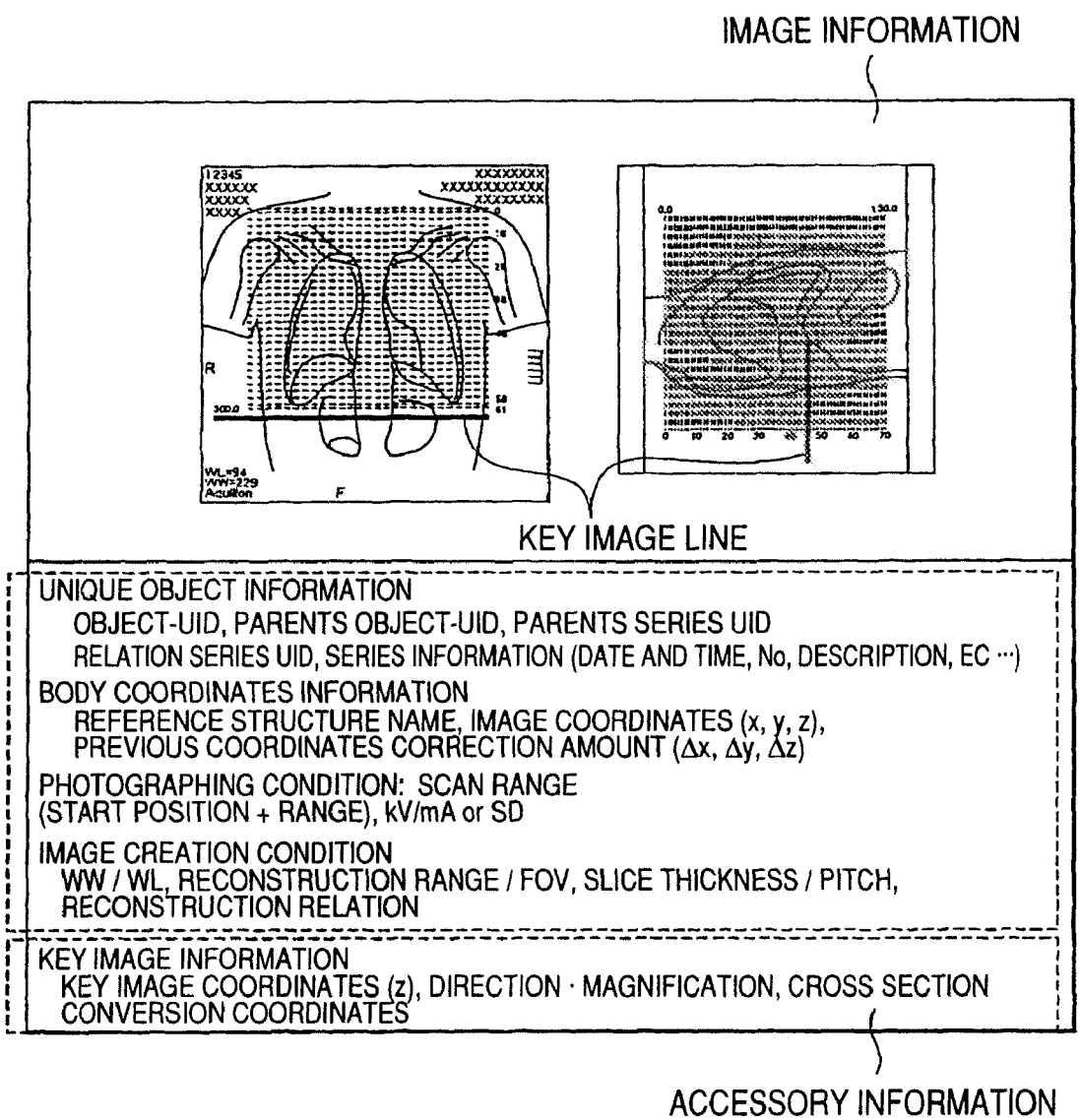
FIG. 5 is a view illustrating an example of the configuration of a shared object.

FIG. 5 is a view illustrating an example of the configuration of a shared object. As shown in the drawing, a shared object is obtained by associating information necessary to reproduce a scan position, an image creating position, and the like as one data integration for the purpose of medical image creation, and the shared object includes image information and accessory information. Hereinafter, the image information and the accessory information included in the shared object will be described.

[Image Information]

Image information included in a shared object is one or a plurality of position determination images (for example, scanogram used in an X-ray CT apparatus or a coronal image due to pilot scan used in an MRI apparatus) for referring to a position or a range. Here, the range refers to a physical range where a detector is to perform signal detection or image creation on the basis of energy that is supplied by the medical image diagnostic apparatus using an X ray or a high frequency. For example, in the case of the X-ray CT apparatus 1, the range is a range (reconstruction range) in the body-axis direction, which is reconstructed on the basis of projection data detected by the detector, and in the case of the MRI apparatus, the range is a scan range. The range is generally expressed by using a dotted line on a position determination image acquired before scan and may be displayed together with lines indicating an image creation pitch in the body-axis direction.

[Accessory Information]

Accessory information included in the shared object may be largely divided into five classes including unique object information, body coordinates information, a photographing condition, an image creating condition, and key image information. Hereinafter, each of the information will be described.

[Accessory Information 1: Unique Object Information]

The unique object information is information for distinguishing corresponding object from other objects or for showing relation with other objects and includes an object identifier (object UID), a parent object identifier (parent object UID), a relation series identifier (relation series UID), and a corresponding series identifier (corresponding series UID).

The object UID is information for distinguishing corresponding object from another object and is numbered by an object creating unit of each apparatus in a system where the information is not repeated at the time of creating a shared object. The parent object UID is information for specifying an object (parent object) referred when creating the corresponding object. The relation series UID is information for specifying series using the same condition (for example, a photographing condition or a position determination condition) as the corresponding shared object. Due to a property of the relation series UID, a plurality of relation series UIDs may exist within the unique object information. At this time, it is preferable to add accessory information (series date and time, series number, series description, type of a used apparatus) of the series in association with the series UID. With such configuration, it is possible to acquire information that an operator identifies only by referring to a shared object, without searching an actual image group. The corresponding series UID is an identifier for specifying series of which a photographing condition or the like is displayed by corresponding shared object.

Further, data specified by each UID has link added thereto. Accordingly, by accessing data at the link location on the basis of each UID, it is possible to quickly search a test flow derived from the image group. In addition, it may be possible to include creation date and time of a shared object in the unique object information.

[Accessory Information 2: Body Coordinates Information]

Body coordinates information refers to information on coordinates (body reference coordinates) based on a structure of a body on an image, unlike a coordinate system (generally, coordinates of each apparatus that uses an absolute bed position or a relative bed position as a reference) that an image group acquired by scan has. The body reference coordinates are created in a shared object creating unit of each apparatus.

Figure 6A:
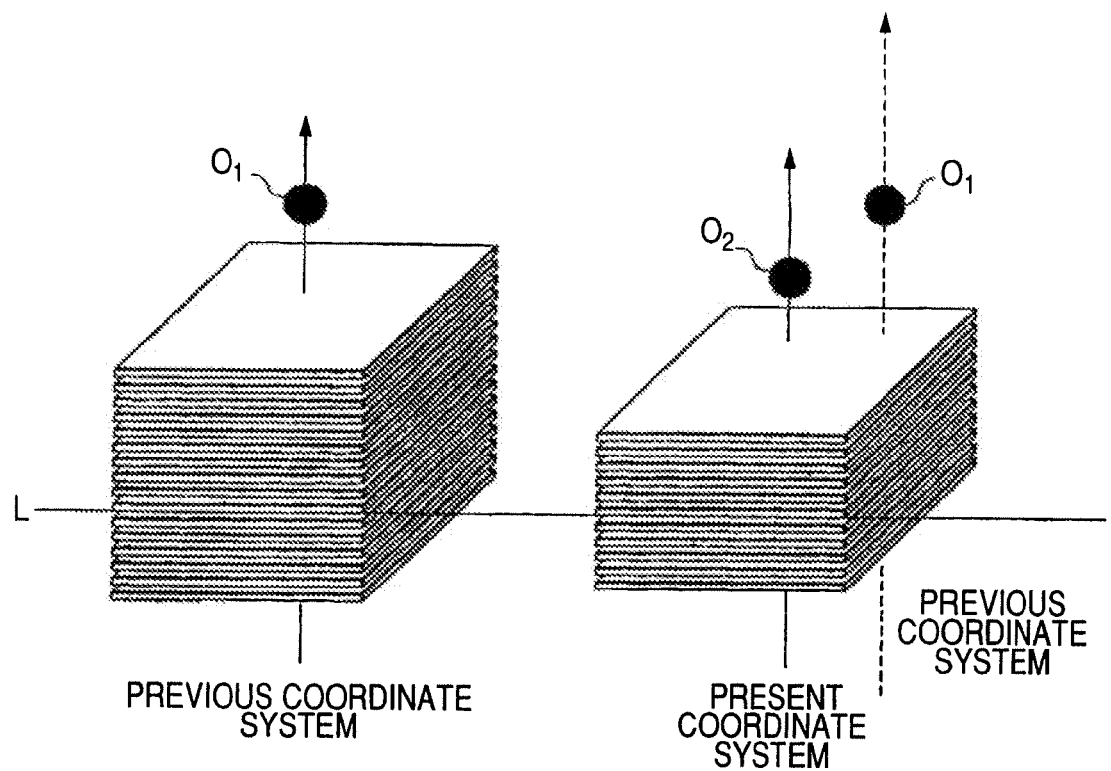
FIG. 6A is a view explaining a concept of body reference coordinates.
Figure 6B:
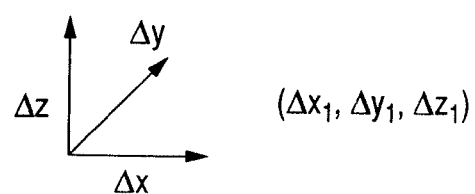
FIG. 6B is a view explaining a concept of body reference coordinates.

FIGS. 6A and 6B are views explaining a concept of body reference coordinates. In the drawings, a tomographic layer apart from a reference point O1 (for example, an OM line, the pelvis, or the pit of the stomach) in a previous body coordinate system by a distance L is assumed to be a tomographic position to be photographed. In the case, it is possible to specify the same position as a tomographic layer, which has been previously photographed, on the basis of a coordinate correction amount ($\Delta x$, $\Delta y$, $\Delta z$), which is a deviation amount between the reference point O1 and a reference O2 (positioned at the same location as the reference point O1 from an anatomic point of view) in a present coordinate system, and the distance L from the reference point. Accordingly, by using the body coordinates information, it is possible to anatomically match the position, such as a photographing range or key image coordinates of key image information, where reproduction is necessary in a next test or image reading.

Further, position information included in the body coordinate information is not limited to the example described above. For example, in addition to the correction amount ($\Delta x$, $\Delta y$, $\Delta z$) of the coordinate system, in the case of performing correction including magnification or rotation, the body coordinates information may include a magnification rate $\alpha$ or a rotation angle ($\beta$, $\theta$) or include a location deviation amount ($\Delta x2$, $\Delta y2$, $\Delta z2$) deviating from a separate reference point without being limited to one reference point.

Furthermore, as a reference point of coordinates, a combination of a name of an anatomical structure and a position determination image coordinate system (an upper left of image data is set to (0, 0)) may be included as information separately from the correction amount described above. The anatomical reference point may be added by providing an image display unit, such as modality or PACS, a function of acquiring and storing position information that an operator designates. When using this, it is possible to show an anatomical reference point on a position determination image in a previous test by means of drawing. When an operator designates the same anatomical structure in a present position determination image while viewing this, a test apparatus can easily recognize a deviation amount (correction amount of coordinate system) with respect to a previous coordinate system.

As the anatomical reference point, it is preferable to select a portion whose location change due to physiological body motion, such as breathing or beating, is small. Specific examples include a center of a lower edge of the twelfth vertebral body, the iliac spine, the iliac crest, a lower edge of pubic symphysis, and a lower edge of an organ-branch portion. Here, names are stored so that a man can decide the structure. However, in the case of using a technique of automatically distinguishing organs within a body on the basis of an image, it is possible to use an identifier of a structure that can be distinguished by a calculator. The technique is researched and disclosed in 'Scientific Research on Priority Areas, Intelligent Assistance in Diagnosis of Multi-dimensional Medical Images (http://www.future-cad.org/fcad/index_j.htm)'.

[Accessory Information 3: Photographing Condition]

A photographing condition is a physical condition required to acquire physical data, which serves as a basis for image creation, from a patient by means of a photographing operation. Details of the condition depend on a type of modality. For example, a photographing condition of an X-ray CT apparatus is a physical amount, such as start position and range (bed movement amount) of scan, KV/mA of an X-ray tube, or a bed movement amount (beam pitch) in one rotation corresponding to an overall width of an obtained image slice. However, details of the photographing condition are not limited to the example. For example, it may be possible to configure to include a tested body insertion direction (information on whether feet is to be inserted first or a head is to be inserted first) at the time of a test, information on whether to use a contrast agent or not, a dosage, a type of medical agent, a body position of a patient (sleeping position or posture in a diagnosis), and the like. Moreover, in recent years, in order to reduce an amount of exposure, there is provided a function of automatically controlling KV/mA so as to have constant image quality. In this case, an image noise (SD value) which is a control amount may be included in a photographing condition.

Further, for example, in the case of an MRI apparatus, the photographing conditions may include parameters, such as a photographing range, insertion direction or body position of a patient, a magnetic field intensity, a pulse sequence, a type of detection coil, a location where the detection coil is provided, information on whether or not there is electrocardiographic synchronization, information on whether or not there is breathing synchronization, information on whether or not there is ventilation for a bed, a body portion serving as a photographing reference, and a mounting position.

[Accessory Information 4: Image Creating Condition]

An image creating condition is a parameter for reconstructing an image from physical data obtained by photographing. For example, the image creating conditions include filter processing parameters, such as a reconstruction range, time phase, a position of an image, direction, thickness, FOV (magnification rate), and a reconstruction function. In addition, the image creating conditions include a condition used in image processing such as volume rendering or MPR process performed in various medical image diagnostic apparatuses or image reference apparatuses. For example, in the case of the MPR process, reference coordinates, a normal vector, a slice thickness, a range, and the like correspond to the conditions.

Moreover, a range of a reconstruction condition may be defined by adding a position determination image showing a reconstruction range. In the above case, a plurality of position determination images showing a plurality of reconstruction ranges are stored in one shared object.

[Accessory Information 5: Key Image Information]

Key image information is a component at the side of a PACS and, for example, information on position, direction, and image processing of a key image added in an image reading step or an image diagnostic step. A shared object creating unit of each apparatus recognizes a corresponding image as a key image at a timing at which a specified image displayed on an image reference apparatus of a PACS is designated as a key image or at a timing at which an operation of adding the specified image into a report or an operation (hyperlink) of associating the specified image with a report sentence is performed. The image reference apparatus searches and specifies a shared object of series including the recognized image. Information including an identifier of the image, for example, SOPInstanceUID based on DICOM standard, a z-axis coordinate position or a direction at the time of observation, a magnification rate, and WW/WL is maintained as key image information. In addition, in the case when an MPR is created, the position, direction, and creating condition with respect to the MPR image, which will be a key image, may be used in the same manner as the image creating condition.

By maintaining the above accessory information, image that can be compared with a previous image can be properly photographed without omission at the start of test imaging. Furthermore, the shared object does not necessarily have all the information shown above. That is, details of the shared object may be changed according to a used apparatus or an intention as long as information used at the time of medical act in the past can be effectively used. For example, a shared object used in a medical image diagnostic apparatus (modality) may be configured to include a patient ID, position information related to a scan range (reconstruction range), accessory information composed of landmarks, and a reference image as image information. Furthermore, a shared object used in a PACS may be configured to include a patient ID, accessory information composed of position information/landmark of a key image, and a reference image as image information. Further, in the case of desiring a means for using only a past photographing condition or the like without needing the reference image, it is preferable to configure the shared object with only accessory information including a photographing condition or the like.

(Operation)

Next, an operation of the medical image diagnostic system S will be described by way of an example in which a shared object is created in the X-ray CT apparatus 1 or the PACS server 9.

First Example

First, a process of creating a shared object in the X-ray CT apparatus 1 will be described. The process of creating a shared object refers to creating a shared object related to corresponding series, for example, at a timing at which an image of the same series is created and stored. However, the timing for creating a shared object is not limited to this example. Any timing may be applied as long as information, such as a photographing condition or an image creating condition, included in a shared object has been determined in the corresponding series.

FIG. 7 is a timing chart illustrating a flow of a process performed by the X-ray CT apparatus 1 in creating a shared object. As shown in the drawing, first, when patient information, such as a patient ID, is input and a test order is selected to acquire an X-ray CT image (step S1), the control unit 127 controls the X-ray tube 113, the X-ray detector 115, and the like on the basis of photographing conditions (for example, FOV, tube voltage, and a scan direction) of scanogram with respect to the corresponding patient so as to acquire scanogram and then displays the acquired scanogram on the display unit 129 (step S2).

Then, when a photographing condition, an image creating condition, and the like are set through the input unit 131 (step S3), the control unit 127 performs a scan for acquiring an X-ray CT image according to the set photographing condition (step S4).

The reconstruction unit 123 creates the X-ray CT image according to the set image creating condition (step S5). The created X-ray CT image is automatically stored in the storage unit 125 as one series information (step S6).

Then, the shared object creating unit 133 creates a shared object and creates information (for example, correspondence table between series UID and shared object UID) related to corresponding series information by using information on series stored in step S6, a photographing condition used in corresponding scan, scanogram, or an image creating condition used in the X-ray CT image creation (step S7).

Furthermore, in the setting of the photographing condition and the image creating condition in step S3, for example, past scanogram with respect to a corresponding patient, an image creating condition, and the like may be referred. In the case, it is preferable to include the corresponding referred past scanogram and a past series UID corresponding thereto in a shared object.

The created shared object and the relation information are transmitted to the PACS server 9 together with series information obtained by the scan, by means of the transmitting and receiving unit 140 (step S8). The PACS server 9 stores the acquired series information in the image storage unit 95*a* and the shared object and the relation information in the shared object storage unit 95*b* (step S9).

Second Example

Next, a process of creating a shared object in the PACS server 9 will be described. The process of creating a shared object refers to, when scan is performed in, for example, an X-ray CT apparatus by referring to past scanogram or the like, creating a shared object by using an image group (and accessory information thereof) forming the series corresponding to the referred scanogram in a state where receiving of image data, a shared object, and relation information from the X-ray CT apparatus serves as trigger.

However, the timing at which the shared object is created is not limited to the example. For example, the PACS server 9 may perform the process of creating a shared object at an arbitrary timing set on the basis of accessory information or the like added in a past image stored in the PACS server 9.

Figure 8:
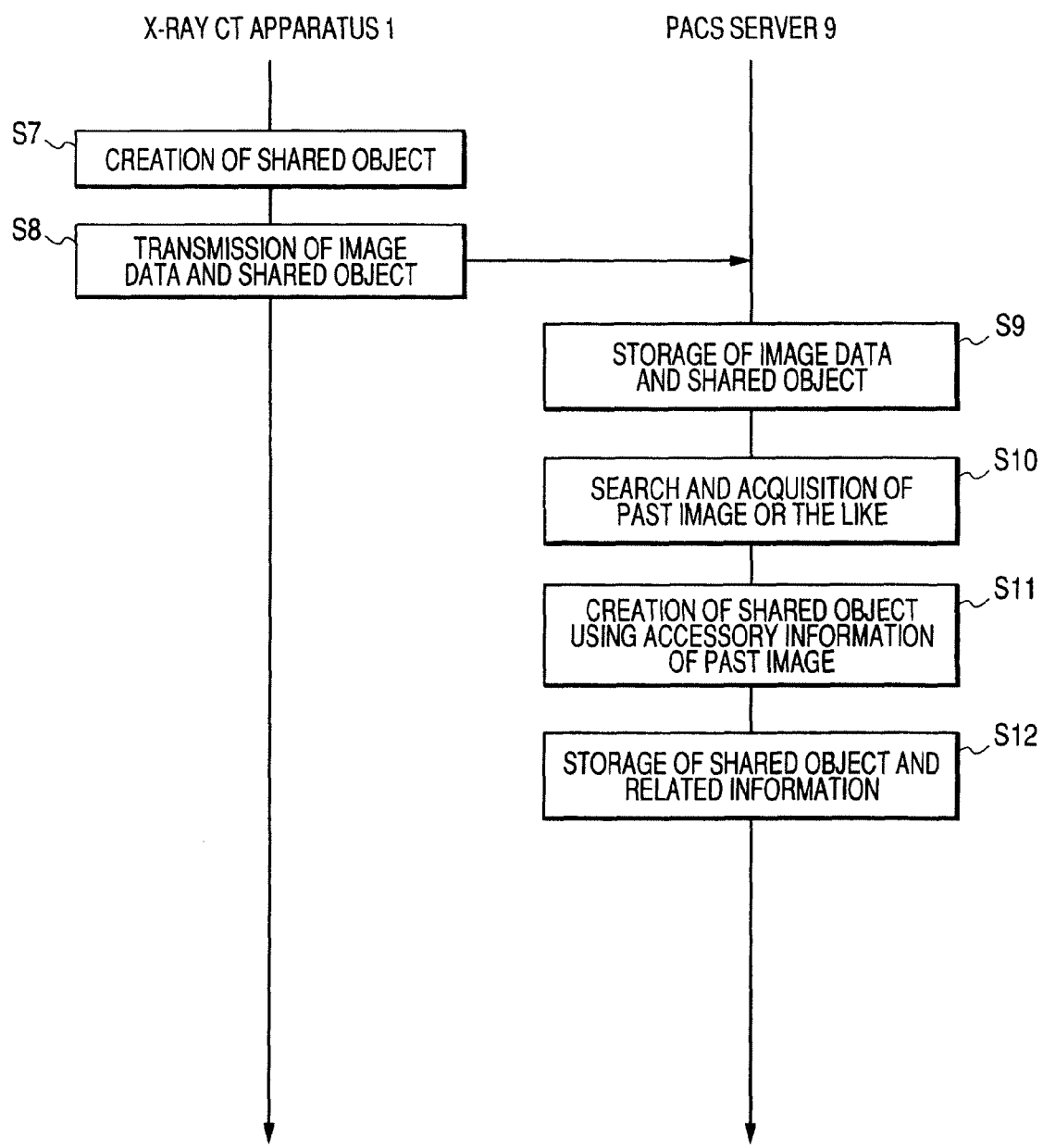
FIG. 8 is a timing chart illustrating a flow of a process performed by the PACS server 9 in creating a shared object.

FIG. 8 is a timing chart illustrating a flow of a process performed by the PACS server 9 in creating a shared object. In addition, Steps S7 to S9 in the drawing are the same as those in FIG. 7.

The shared object creating unit 92 searches and acquires a past image (including a position determination image), past photographing information, and the like referred in the scan corresponding to the received series, on the basis of the related series UID (step S10). Then, the shared object creating unit 92 creates a shared object by using accessory information of the acquired past image, the position determination image, and the like and creates relation information between the shared object and the past image (step S11). The created shared object and the relation information are stored in the shared object storage unit 95*b* (step S12).

Third Example

Next, a process of creating a shared object in the image reference apparatus 7 will be described. The process of creating a shared object refers to creating a shared object by using the setting of image processing parameters used for creation of a key image in, for example, an image reading step, the position of the key image within a photographing range, and the like.

Figure 9:
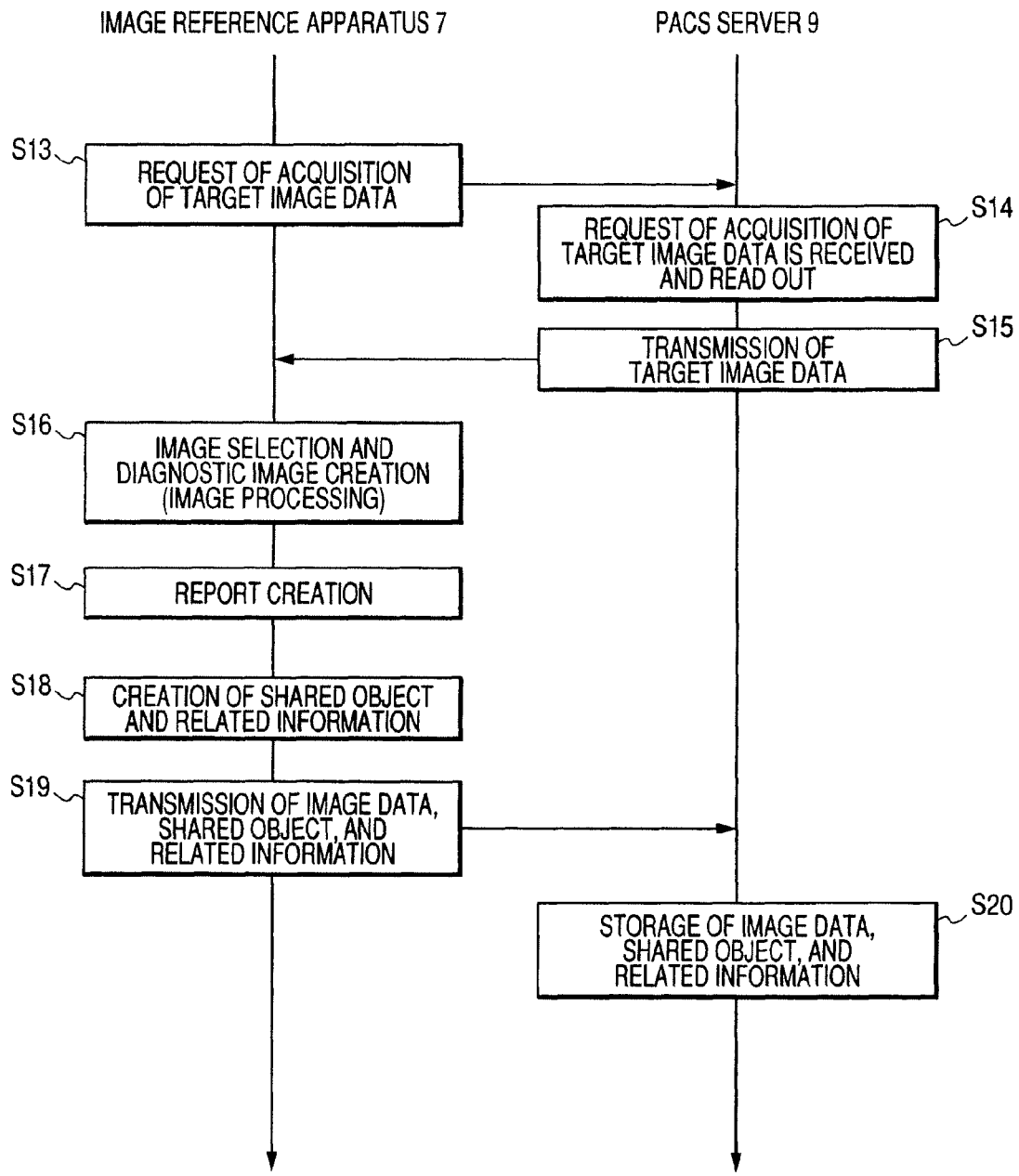
FIG. 9 is a timing chart illustrating a flow of a process performed by the image reference apparatus 7 in order to create a shared object.

FIG. 9 is a timing chart illustrating a flow of a process performed by the image reference apparatus 7 in creating a shared object. As shown in the drawing, first, the control unit 71 transmits to the PACS server 9 a request for acquisition of an image data group belonging to the series to be read, in order to perform an image reading process (step S13). The control unit 91 of the PACS server 9 receives the acquisition request and reads out a corresponding image data group from the image storage unit 95*a* (step S14). The read image data group is transmitted to the image reference apparatus 7 by the transmitting and receiving unit 96 (step S15). The transmitted image data group is transmitted to the transmitting and receiving unit 78 of the image reference apparatus 7 and is then stored in the storage device 77.

Then, a doctor who reads an image selects a key image from the image data group, and predetermined image processing on the key image is performed by the image processing unit 72 according to an instruction from the operation unit 74 (step S16). The report creating unit 75 creates a report on the basis of an input of the image-reading doctor through the operation unit 74 (step S17).

Then, the shared object creating unit 76 creates a shared object and information related with a corresponding report by using a condition (for example, magnification rate and a conversion process) on image processing performed in step S17, position information for specifying a key image, and a UID of series to be read (step S18).

Moreover, in the key image selection in step S16, the acquired position determination image may be referred in the series to be read. In the case, it is preferable to configure to include the referred position determination image in the shared object.

The created shared object and the relation information are transmitted to the PACS server 9 together with the created report by the transmitting and receiving unit 140 (step S19). The PACS server 9 stores the acquired report in the report storage unit 95*d* and the shared object and the relation information in the shared object storage unit 95*b* (step S20).

According to the configuration described above, the following effects can be obtained.

According to the medical image diagnostic system, shared information (shared object) is newly created in a unified format with respect to some of past medical information, which is effective in a photographing step or a report creating step. The shared object includes a position determination image, unique object information, body coordinates information, a photographing condition, an image creating condition, and key image information. Thus, at the time of present photographing, a past (for example, previous) photographing condition or photographing range can be reproduced with high precision.

Further, the shared object formed in the medical image diagnostic system is created in the unified format. Therefore, since deviation does not occur in the shared object, the medical image diagnostic system has high versatility. As a result, the medical image diagnostic system can be used in a variety of apparatuses or processes.

Furthermore, the shared object formed in the medical image diagnostic system includes, as unique object information, information on corresponding series or information for specifying (parent) shared object serving as a basis of creation. Therefore, it is possible to quickly access the shared object or the information corresponding to the series.

In addition, in the medical image diagnostic system, automatic creation is made at a predetermined timing, such as series information creation, by using a photographing condition used in the corresponding apparatus. Therefore, it is possible to create shared information, which is effective for a medical act, without requesting a photographer of a new work.

In addition, in the present embodiment, an example has been shown in which each of the X-ray CT apparatus 1, the PACS server 9, and the image reference apparatus 7 has a function of creating a shared object. However, the invention is not limited thereto. For example, at least one of the X-ray CT apparatus 1, the PACS server 9, and the image reference apparatus 7 may have the function of creating a shared object. That is, the configuration may be changed in various forms according to utilization purpose.

Second Embodiment

Next, a second embodiment of the present invention will be described. A medical image diagnostic system S according to the present embodiment has a support function (hereinafter, referred to as a 'support function using a shared object') of simplifying access to past information (for example, a key image at the time of a previous test) used in condition setting and image reading (and report creation accompanied thereby) of various medical-related apparatuses, which are used for an image diagnosis, using the shared object created by the method described in the first embodiment, for example.

Figure 10:
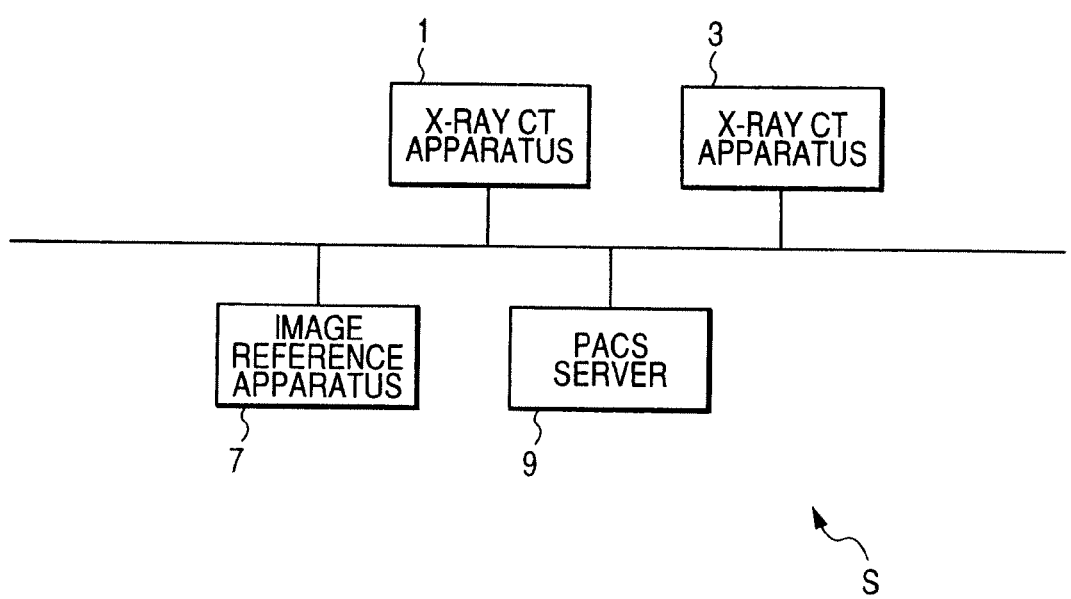
FIG. 10 is a view illustrating the configuration of a medical image diagnostic system S according to a second embodiment.

FIG. 10 is a view illustrating the configuration of the medical image diagnostic system S according to the present embodiment. When the configuration shown in the drawing is compared with that in FIG. 1, the configuration shown in the drawing is different from that in FIG. 1 in that an X-ray CT apparatus 3 having a support function using a shared object is further provided and the image reference apparatus 7 has a support function using a shared object.

[X-Ray CT Apparatus]

Figure 11:
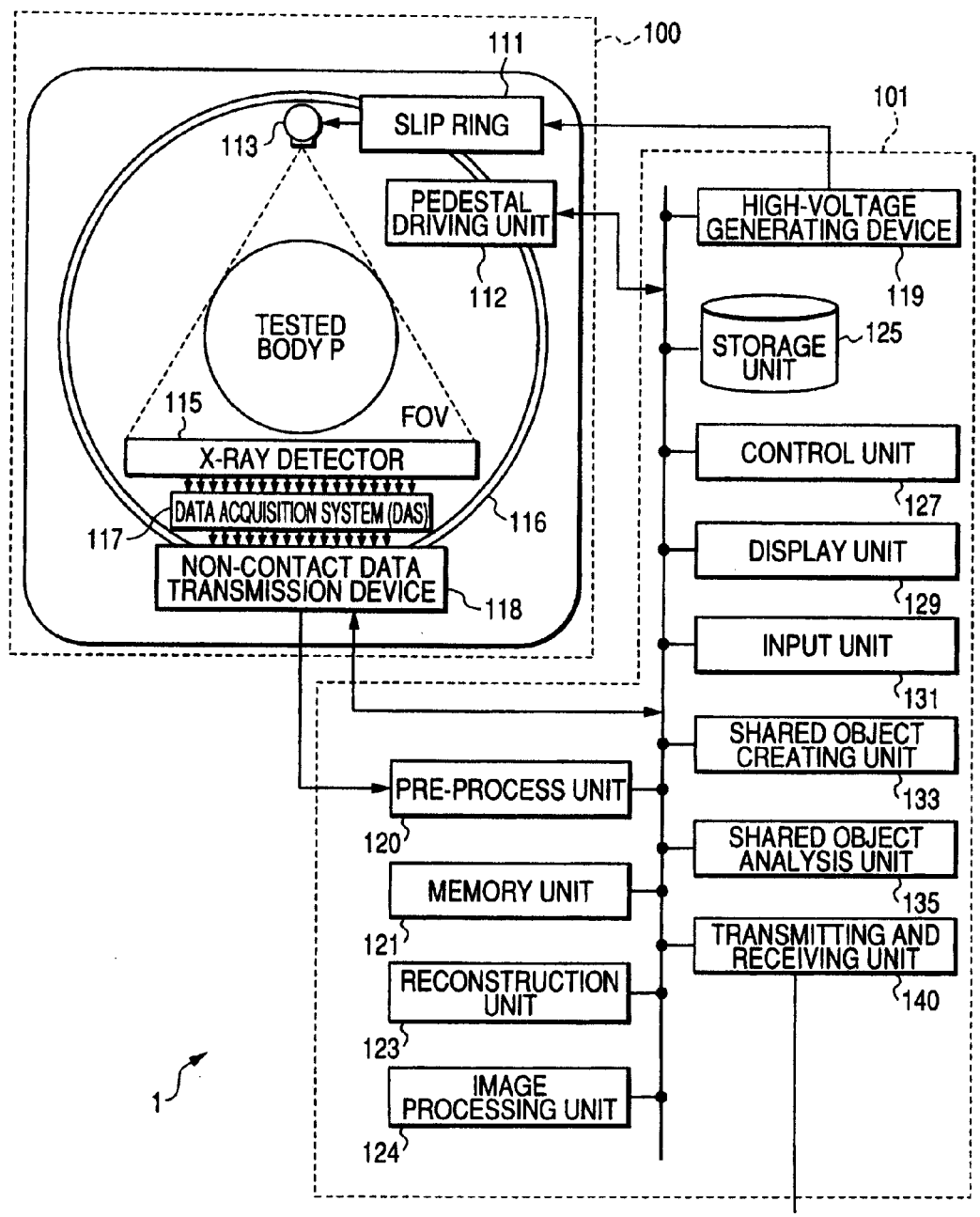
FIG. 11 is a view illustrating the configuration of an X-ray CT apparatus 3 according to the second embodiment.

FIG. 11 is a view illustrating the configuration of the X-ray CT apparatus 3 according to the present embodiment. The configuration of the X-ray CT apparatus 3 shown in the drawing is different from the configuration of the X-ray CT apparatus 1 shown in FIG. 2 in that a shared object analysis unit 135 is further provided and a support function using a shared object is further provided.

The storage unit 125 stores a dedicated program for realizing a support function using a shared object, which will be described later.

The control unit 127 loads a dedicated program into a memory (not shown) so as to realize a support function using a shared object. This will be described in detail later.

The shared object analysis unit 135 analyzes, for example, a shared object read from the shared object storage unit 95b within the PACS server 9 in a process (support function using a shared object) based on a support function using a shared object.

[Image Reference Apparatus]

Figure 12:
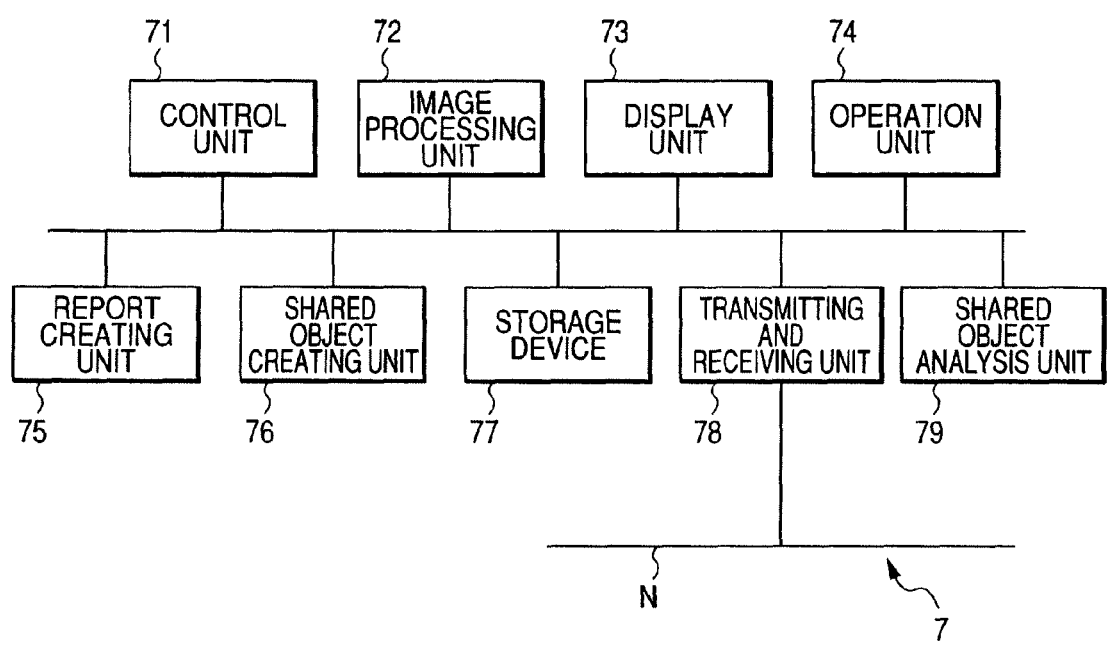
FIG. 12 is a view illustrating the configuration of an image reference apparatus 7 according to the second embodiment.

FIG. 12 is a view illustrating the configuration of an image reference apparatus 7 according to the present embodiment. The configuration of the image reference apparatus 7 shown in the drawing is different from that of the image reference apparatus according to the first embodiment shown in FIG. 3 in that a shared object analysis unit 79 is further provided and a support function using a shared object is further provided.

The storage unit 77 stores a dedicated program for realizing a support function using a shared object, which will be described later.

The control unit 71 loads a dedicated program stored in the storage unit 77 into a memory (not shown) so as to realize a support function using a shared object. This will be described in detail later.

The shared object analysis unit 79 analyzes, for example, a shared object read from the shared object storage unit 95b within the PACS server 9 in a support process using a shared object.

(Support Function Using a Shared Object)

Next, it will be described about an operation of the medical image diagnostic system S when each of the X-ray CT apparatus 3 and the image reference apparatus 7 performs a support process using a shared object.

First Example

First, it will be described about an operation of the medical image diagnostic system S when the X-ray CT apparatus 3 performs a support process using a shared object. The support function using a shared object is, for example, to support a work, such as photographing condition setting and photographing range setting, at the time of photographing by using a shared object related to series acquired in the past test of the same patient.

Figure 13:
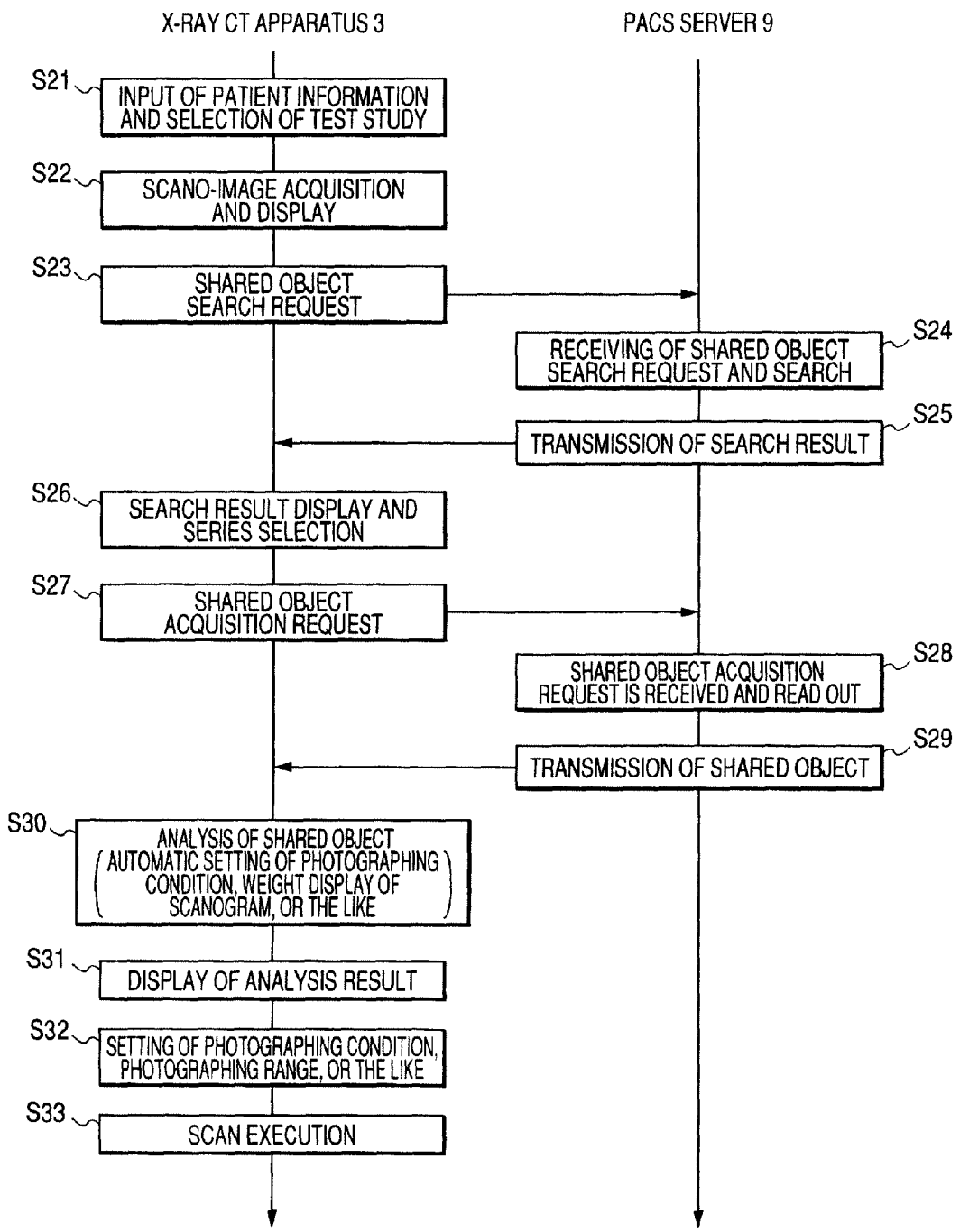
FIG. 13 is a timing chart illustrating a flow of a process of the medical image diagnostic system S when performing a support process using a shared object.
Figure 14:
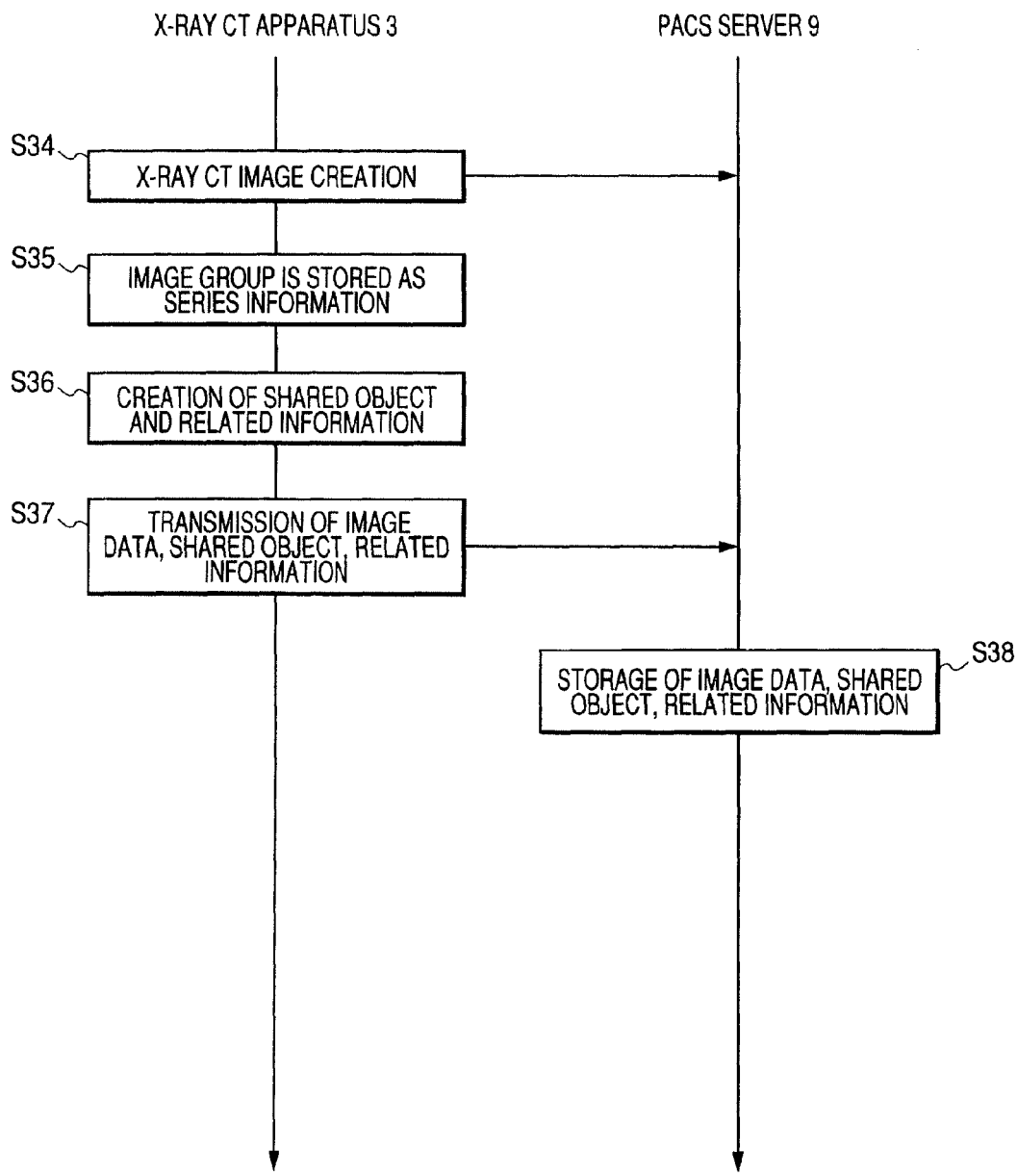
FIG. 14 is a timing chart illustrating a flow of a process of the medical image diagnostic system S when performing a support process using a shared object.

FIGS. 13 and 14 are timing charts illustrating a flow of a process of the medical image diagnostic system S when performing a support process using a shared object. As shown in the drawings, first, when patient information, such as a patient ID, is input and a test order is selected to acquire an X-ray CT image (step S21), the control unit 127 controls the X-ray tube 113, the X-ray detector 115, and the like on the basis of photographing conditions of scanogram so as to acquire scanogram with respect to the corresponding patient and then displays the acquired scanogram on the display unit 129 (step S22).

Then, the control unit 127 transmits to the PACS server 9 through the network N a search request for a shared object corresponding to series information of the patient on the basis of patient information input in step S21 (step S23). In response to the search request, the control unit 91 of the PACS server 9 searches a shared object of series related to the corresponding patient among shared objects stored in the shared object storage unit 95b (step S24) and transmits a result of the search to the X-ray CT apparatus 3 (step S25). The search result transmitted to the transmitting and receiving unit 140 of the X-ray CT apparatus 3 is displayed on the display unit 129 in a predetermined form.

Figure 15:
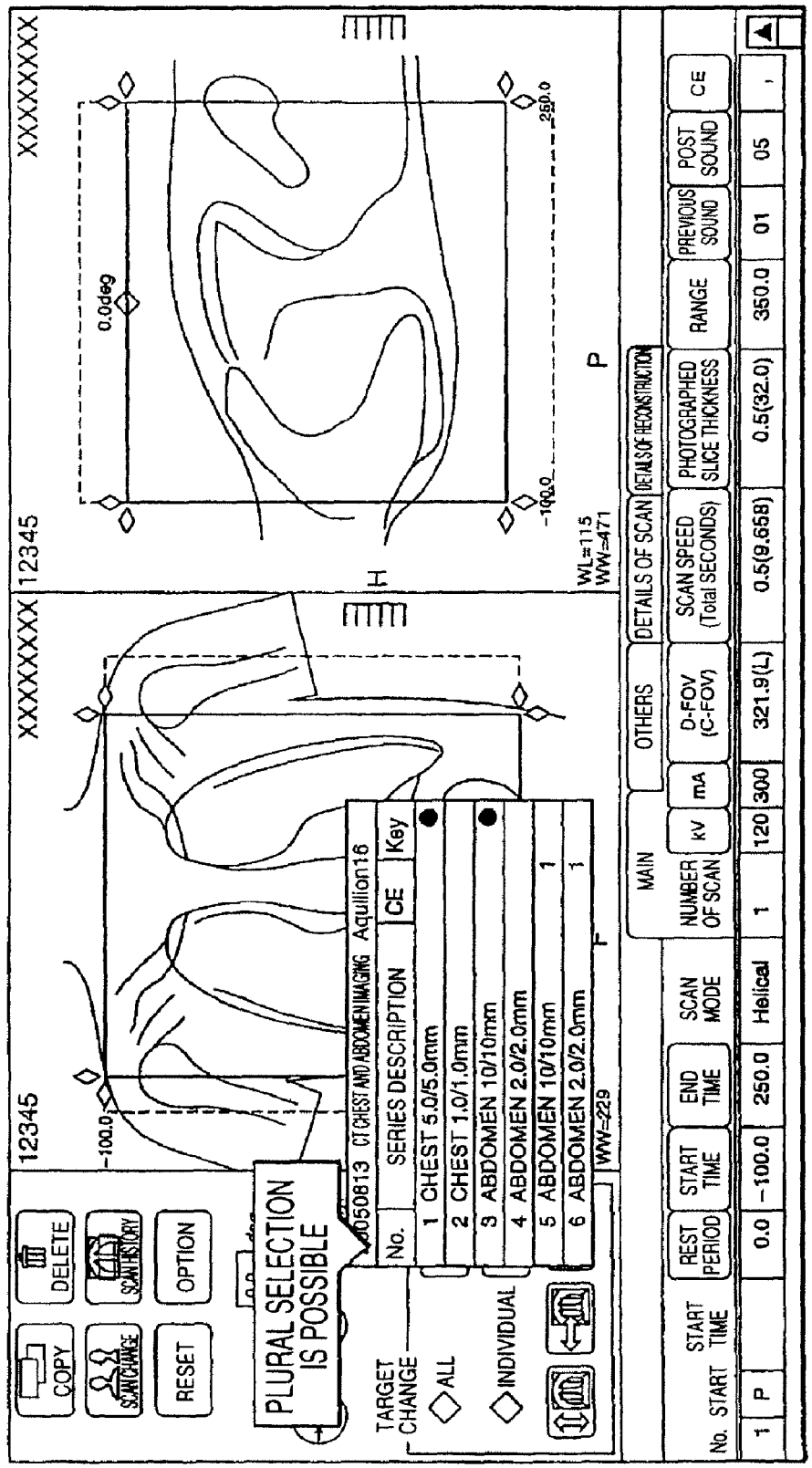
FIG. 15 is a view illustrating an example of a display pattern of a shared object analysis result.
Figure 16:
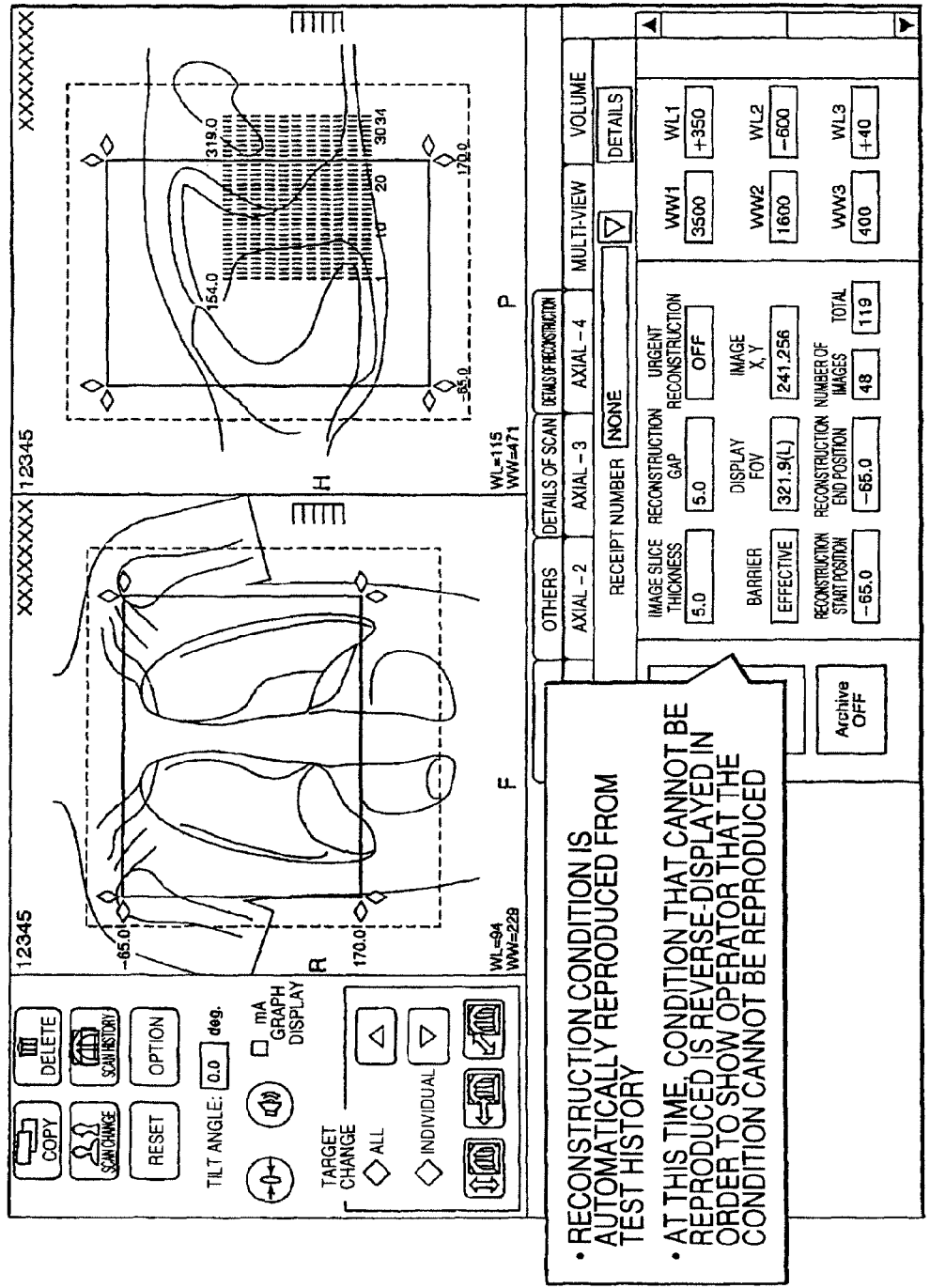
FIG. 16 illustrates a display pattern of a search result of a shared object corresponding to series information of a patient, where an example is shown in which the series information of the patient is displayed in the form of a list.

FIG. 15 illustrates a display pattern of the search result of a shared object corresponding to series information of a patient, where an example is shown in which the series information of the patient is displayed in the form of a list. When an operator selects desired series from a plurality of series information, which is displayed in the form of a list, through the input unit 131 (step S26), the control unit 127 transmits to the PACS server 9 an acquisition request for a shared object corresponding to the selected series through the network N (step S27). In response to the acquisition request for the shared object, the control unit 91 of the PACS server 9 extracts a shared object corresponding to the series selected from the shared object storage unit 95b (step S28) and then transmits the extracted shared object to the X-ray CT apparatus 3 through the network (step S29).

The shared object transmitted to the transmitting and receiving unit 140 of the X-ray CT apparatus 3 is analyzed in the shared object analysis unit 135 (step S30). That is, the shared object analysis unit 135 analyzes a photographing condition recorded in the acquired shared object and makes automatic setting such that a condition consistent with present photographing is equal to that of the corresponding shared object. In addition, the shared object analysis unit 135 analyzes a past position determination image included in the shared object and specifies a reference point (for example, a landmark on a body) on a corresponding image and a reference point on a present (that is, acquired in step S22) position determination image. In addition, the reference point designation of the past and present position determination images is not limited to the above example. For example, the reference point designation of the past and present position determination images may be manually performed.

The control unit 127 displays an analysis result of a shared object on the display unit 129 in a predetermined form (step S31). Specifically, the control unit 127 displays the analysis result on the display unit 129, for example, in the form of dialog shown in FIG. 15 so that a condition determined to be inconsistent with the present photographing by the shared object analysis can be set and it is possible to determine the availability of the automatically set condition. In addition, the control unit 127 displays both position determination images so as to overlap each other or be adjacent to each other, such that the reference point on the present position determination image and the reference point on the past position determination image included in the shared object correspond to each other.

Then, the control unit 127 sets a photographing range and the other conditions determined be inconsistent with the present photographing by the shared object analysis on the basis of an operator's instruction made through the input unit 131 (step S32). At this time, since the past and present position determination images are displayed such that the reference points thereof correspond to each other, the operator can more precisely recognize a setting difference between the past and the present. Accordingly, the operator can perform cross section setting in the present test such that the position of an anatomical cross section matches that in the past test, in consideration of the difference. Moreover, the cross section setting in step S32 may be automatically performed on the basis of body coordinates information by an apparatus, in addition to the manual operation of an operator.

Then, when a photographing condition, an image creating condition, and the like are set through the input unit 131, the control unit 127 performs a scan for acquiring an X-ray CT image according to the set photographing condition (step S33). The reconstruction unit 123 creates the X-ray CT image according to the set image creating condition (step S34). The created X-ray CT image is automatically stored in the storage unit 125 as one series information (step S35).

Then, the shared object creating unit 133 creates a shared object and creates information related to corresponding series by using information on series stored in step S6, a photographing condition used in the corresponding scan, scanogram, or an image creating condition used in the X-ray CT image creation (step S36). At this time, a UID of the series selected in step S26 is recorded in the corresponding shared object as a parent series UID used as a reference for the series, and a UID of the shared object in step S27 is recorded in the corresponding shared object as a parent shared object UID selected in step S27.

The created shared object and the relation information are transmitted to the PACS server 9 together with series obtained by the scan, by means of the transmitting and receiving unit 140 (step S37). The PACS server 9 stores the acquired series information in the image storage unit 95a and the shared object and the relation information in the shared object storage unit 95b (step S38).

Further, in the present embodiment, it has been described about a case in which positional alignment is automatically performed such that the reference point on the past position determination image and the reference point on the present position determination image correspond to each other. However, the positional alignment or fine adjustment may be made by a manual operation without being limited to the above example.

Furthermore, the positional alignment between position determination images is performed, for example, on the basis of the position of bones on an image. Accordingly, for example, by displaying bones imaged on a past position determination image in a green color and an organ in a red color, it is possible to easily perform positional alignment between the past position determination image and a present position determination image displayed in a gray scale.

In addition, in the case of setting a photographing range, it is important to recognize the position of a past key image on the present position determination image. However, in general, even when the same part (or the same range) is photographed, the position thereof may not match between the past position determination image and the present position determination image in a precise sense due to body motion, such as breathing. In order to solve the problem described above, in the case of performing the positional alignment with respect to the past position determination image and the present position determination image, it is preferable to indicate the position of a past key image on the past position determination image with mark display, for example. As described above, by expressing the key image position on the past position determination image, a user can set a present photographing range so as to necessarily include the past key image position.

Second Example

Next, it will be described about an operation of the medical image diagnostic system S when the image reference apparatus 7 performs a support process using a shared object. The support function using a shared object is, for example, to support a work, such as key image searching in a previous test in the image reading step and the same image processing parameter setting as in the previous test, for example, by using a shared object related to series acquired in the past test of the same patient.

Figure 17:
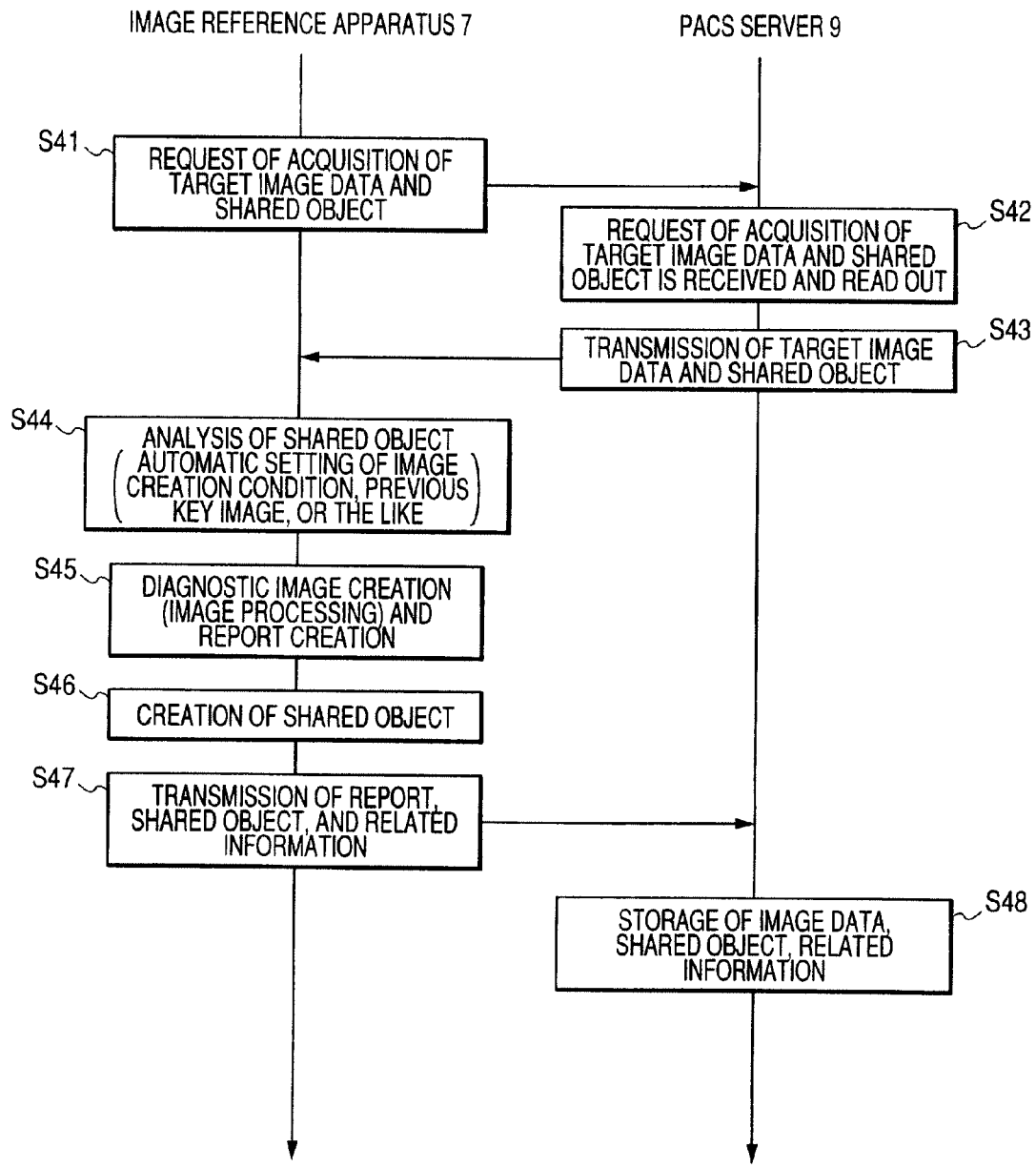
FIG. 17 is a timing chart illustrating a flow of a process of the medical image diagnostic system S when performing a support process using a shared object.

FIG. 17 is a timing chart illustrating a flow of a process of the medical image diagnostic system S when performing a support process using a shared object. As shown in the drawing, first, the control unit 71 transmits to the PACS server 9 a request for acquisition of an image data group belonging to series to be read, a shared object corresponding to the series, and a shared object corresponding to a most recent report on the same test of the patient, in order to perform an image reading process (step S40). The control unit 91 of the PACS server 9 receives the acquisition request, reads the corresponding image data group from the image storage unit 95*a*, reads the corresponding shared object from the shared object storage unit 95*b* (step S42), and transmits a result of the search to the image reference apparatus 7 (step S43).

The shared object transmitted to the transmitting and receiving unit 78 of the image reference apparatus 7 is analyzed in the shared object analysis unit 79 (step S44). That is, the shared object analysis unit 79 analyzes the image creating condition and the like recorded in the acquired shared object, selects an image, which corresponds to the same position as a key image used in creating a previous report, from the received image data group, and automatically sets a image processing parameter used in creating the previous report.

Then, a doctor who reads an image selects a key image from the image data group, and predetermined image processing on the corresponding key image is performed by the image processing unit 72 according to an instruction from the operation unit 74 (step S45). The report creating unit 75 creates a report on the basis of an input of the image-reading doctor through the operation unit 74 (step S45).

Then, the shared object creating unit 76 creates a shared object and information related with a corresponding report by using a condition (for example, magnification rate, direction, and conversion process) on image processing performed in step S17, position information for specifying a key image, a UID of series to be read, and a UID of a shared object analyzed in step S44 (step S46).

The created report, shared object, and relation information are transmitted to the PACS server 9 together with the created report by the transmitting and receiving unit 140 (step S47). The PACS server 9 stores the acquired report in the report storage unit 95*d* and the shared object and the relation information in the shared object storage unit 95*b* (step S48).

According to the configuration described above, the following effects can be obtained.

First, according to the medical image diagnostic system, it is possible to automatically set a photographing condition, a photographing range, a tomographic position to be photographed, or an image creating condition, which are the same as those in a past test, by using a shared object having a unified format. Therefore, it is possible to alleviate a labor of a doctor or the like in a photographing step or a report creating step and to reproduce a condition in a past test (for example, previous test) with high precision.

Further, according to the medical image diagnostic system, a separate setting request for the condition and the like inconsistent with the present setting is made to an operator and a confirmation request on the automatically set condition is also made to the operator. Accordingly, it is possible to prevent erroneous setting on a variety of conditions and to secure high safety while alleviating the labor of a doctor or the like.

Furthermore, according to the medical image diagnostic system, it is possible to display the past position determination image and the present position determination image so as to be parallel to each other or overlap each other by using the body coordinates information of a shared object, such that the past position determination image and the present position determination image spatially coordinate with each other. Accordingly, a doctor or the like can easily recognize and set the photographing range and the position of a cross section to be photographed, and it is possible to realize high-precision image diagnosis while alleviating the labor of a doctor or the like.

In addition, the shared object used by the medical image diagnostic system S is linked with related series or a shared object through unique object information. Accordingly, it is possible to quickly access desired related information, to reduce a labor of a doctor or the like, and to improve working efficiency.

Third Embodiment

Next, a third embodiment of the present invention will be described. A medical image diagnostic system S according to the present embodiment includes a magnetic resonance imaging apparatus (MRI apparatus) using a shared object.

Figure 18:
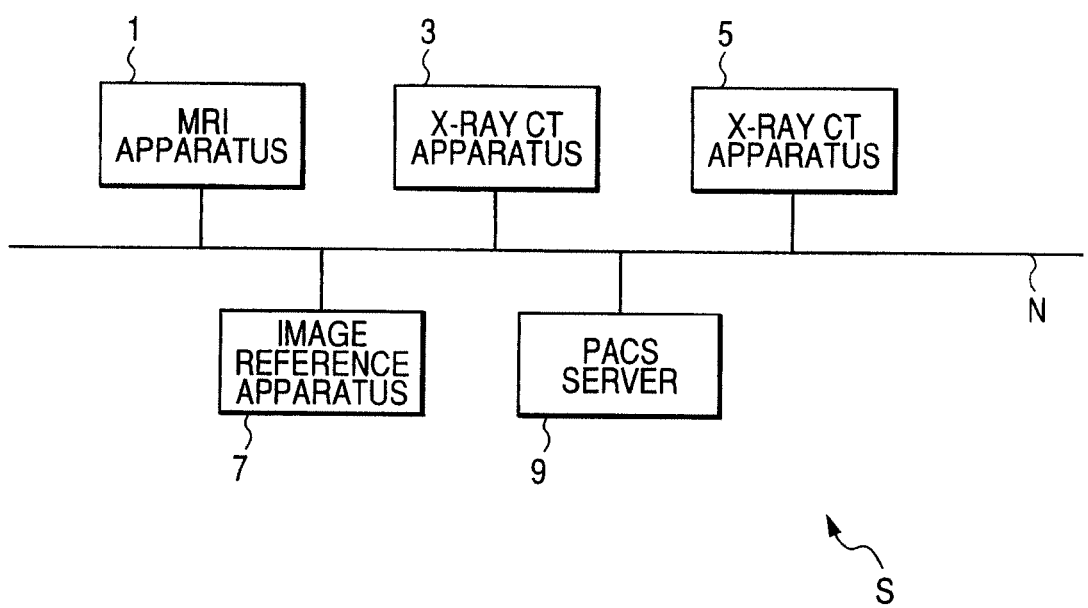
FIG. 18 is a view illustrating the configuration of the medical image diagnostic system S according to the present embodiment.

FIG. 18 is a view illustrating the configuration of the medical image diagnostic system S according to the present embodiment. When the configuration shown in the drawing is compared with that in FIG. 10, the configuration shown in the drawing is different from that in FIG. 10 in that an MRI apparatus 5 having a shared object creating function and a support function using a shared object is further provided.

[MRI Apparatus]

The MRI apparatus 5 creates an image (MR image) on a predetermined cross section of a tested body by performing scan sequences using a magnetic resonance phenomenon.

Figure 19:
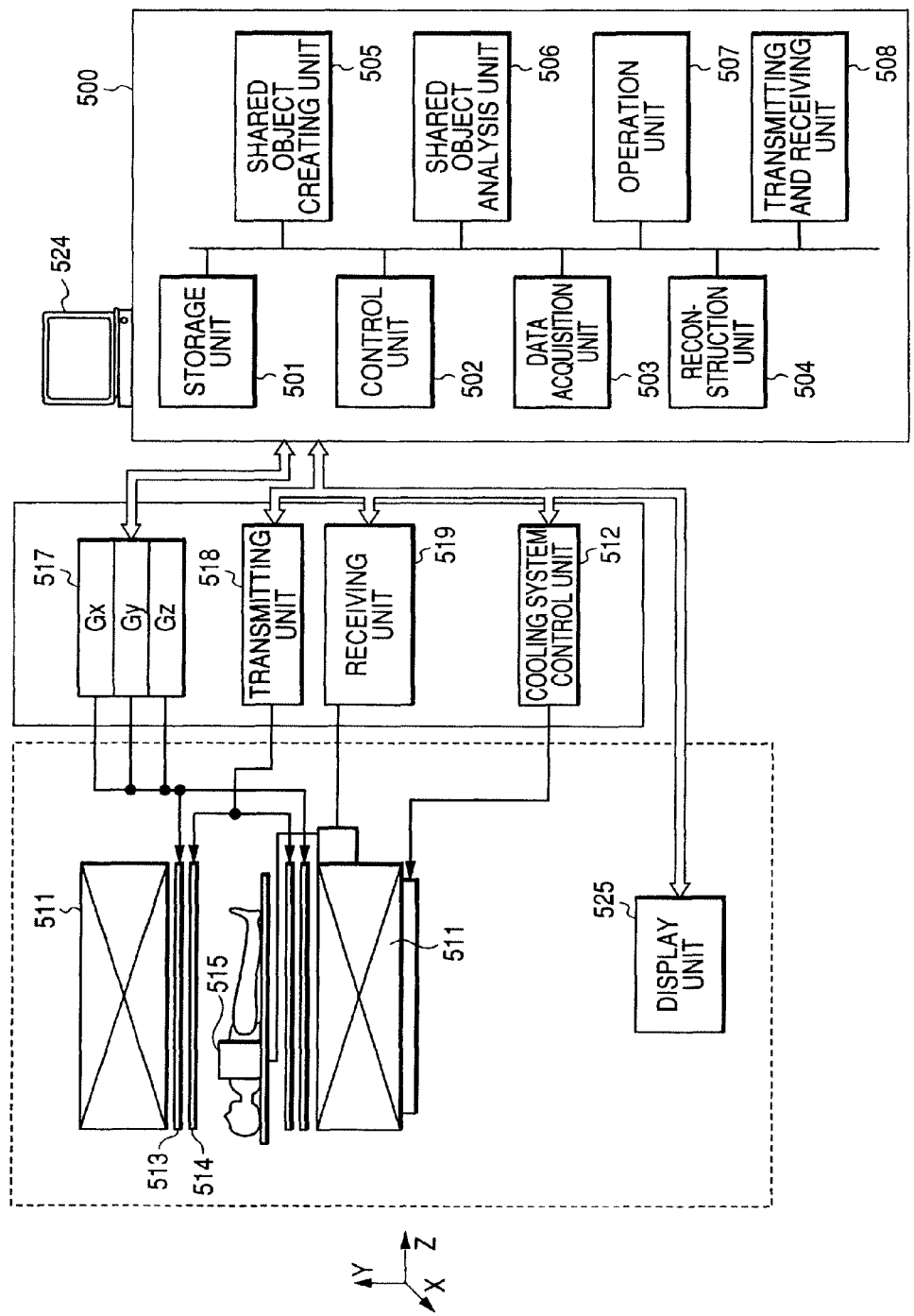
FIG. 19 is a block diagram illustrating the configuration of an MRI apparatus 5 according to a third embodiment.

FIG. 19 is a block diagram illustrating the configuration of the MRI apparatus 5. As shown in the drawing, the MRI apparatus 5 includes a magnetostatic field magnet 511, a cooling system control unit 512, an inclined magnetic coil 513, a high-frequency transmission coil 514, a high-frequency receiving coil 515, a transmitting unit 518, a receiving unit 519, a data processing unit 500, a first display unit 524, and a second display unit.

The magnetostatic field magnet 511 is a magnet that generates a magnetostatic field and generates the same magnetostatic field.

The cooling system control unit 512 controls a cooling mechanism of the magnetostatic field magnet 511.

The inclined magnetic coil 513 is provided inside the magnetostatic field magnet 511, is shorter than the magnetostatic field magnet 511, and converts a pulse current supplied from an inclined magnetic coil device power 517 into an inclined magnetic field. By the inclined magnetic field generated by the inclined magnetic coil 513, a signal generation part (position) is specified.

Further, in the present embodiment, a Z-axis direction is the same direction as a direction of a magnetostatic field. Furthermore, in the present embodiment, the inclined magnetic coil 513 and the magnetostatic field magnet 511 have cylindrical shapes. In addition, the inclined magnetic coil 513 is disposed in a vacuum by a predetermined support mechanism. This is to cause vibration of the inclined magnetic coil 513 generated by application of a pulse current not to propagate as a sound wave to the outside, from the point of view of silence.

The high-frequency transmission coil (RF transmission coil) 514 is a coil for applying a high-frequency pulse to a scan region of a tested body, the high-frequency pulse being used to generate a magnetic resonance signal. The high-frequency transmission coil 514 is a body RF coil. For example, in the case of photographing the abdomen, the high-frequency transmission coil 514 may be used as a receiving coil.

The high-frequency receiving coil (RF receiving coil) 515 is provided in the vicinity of a tested body, preferably, provided such that the tested body is interposed therebetween while being positioned to be close to each other. The high-frequency receiving coil 515 is a coil for receiving magnetic resonance from the tested body. The high-frequency receiving coil 515 generally has a special shape corresponding to each part.

Moreover, in FIG. 19, there is shown a cross coil method in which the high-frequency transmission coil and the high-frequency receiving are separately provided. However, a single coil method in which the high-frequency transmission coil and the high-frequency receiving are provided as one coil may be adopted.

The inclined magnetic coil device power 517 generates a pulse current for forming an inclined magnetic field and supplies the pulse current to the inclined magnetic coil 513. In addition, the inclined magnetic coil device power 517 controls a polarity of the inclined magnetic field by changing the direction of a pulse current supplied to the inclined magnetic coil 513 according to the control of a control unit 502 to be described later.

The transmitting unit 518 includes an oscillation unit, a phase selection unit, a frequency converter, an amplitude modulation unit, a high-frequency power amplification unit (all of which are not shown), and transmits a high-frequency pulse corresponding to the Larmor frequency to a high-frequency coil for transmission. Due to the high frequency generated by the high-frequency transmission coil 514 that has been transmitted, magnetization of a predetermined atomic nucleus of the tested body is in en excited state.

The receiving unit 519 includes an amplification unit, an intermediate frequency conversion unit, a phase detection unit, a filter, and an A/D converter (all of which are not shown). The receiving unit 519 performs an amplifying process, an intermediate frequency converting process using an oscillating frequency, a phase detecting process, a filtering process, and an A/D converting process with respect to a magnetic resonance signal (high-frequency signal) emitted when the magnetization of a nucleus received through the high-frequency receiving coil 515 is reduced from the excited state to a ground state.

The data processing unit 500 is a calculator system that generates a magnetic resonance image by processing received data and includes a storage unit 501, a control unit 502, a data acquisition unit 503, a reconstruction unit 504, a shared object creating unit 505, a shared object analysis unit 506, an operation unit 507, and a transmitting and receiving unit 508.

The storage unit 501 stores an MR image, a position determination image (scout image), and a variety of information acquired through the network N, which are acquired by the MRI apparatus 5. In addition, the storage unit 501 stores a dedicated program for realizing a shared object creating function and a support function using a shared object.

The control unit 502 includes, for example, a CPU and a memory (not shown) and serves as a main control center that controls the magnetic resonance imaging apparatus in a static or dynamic manner. In addition, the control unit 502 loads a dedicated program into a memory (not shown) so as to realize the shared object creating function and the support function using a shared object.

The data acquisition unit 503 acquires digital signals sampled by the receiving unit 519.

The reconstruction unit 504 performs a post process, that is, reconstruction such as Fourier transformation with respect to the data acquired by the data acquisition unit 503, thereby obtaining image data or spectrum data of a nuclear spin within the tested body.

The shared object creating unit 505 creates a shared object including photographing conditions (TR, TE, slice thickness, FOV size, matrix size, and the like) and a position determination image used in magnetic resonance imaging. In addition, the shared object creating unit 76 creates a shared object including an image creating condition or the like used when reconstructing an image on the basis of projection data acquired by scan.

The shared object analysis unit 506 analyzes, for example, a shared object read from the shared object storage unit 95b within the PACS server 9 in a support process using a shared object.

The operation unit 507 includes an input unit (mouse, trackball, mode-switching switch, a keyboard, and the like) for receiving various instruction and command information from an operator.

The transmitting and receiving unit 508 transmits/receives medical information, such as an image or a shared object, to/from other apparatuses through the network N.

The first display unit 524 is an output unit that displays image data or spectrum data input from the data processing unit 500.

Figure 20:
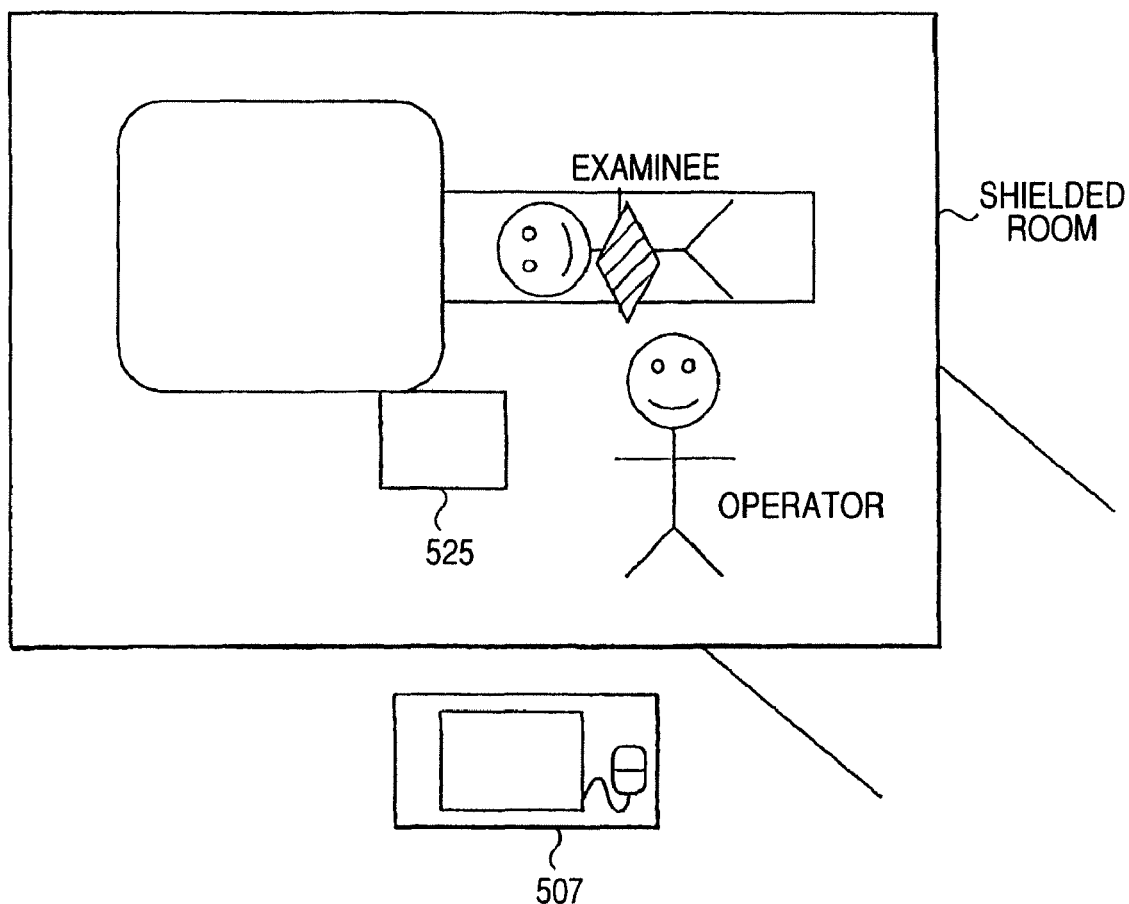
FIG. 20 is a view illustrating an example in which a second display unit 525 is disposed.

The second display unit 525 is disposed, for example, as shown in FIG. 20, within a shielded room where the magnetostatic field magnet 511, the inclined magnetic coil 513, and the like are disposed, or the second display unit 525 is disposed at another predetermined position viewable from the shield room. In addition, the second display unit 525 displays, for example, photographing information (for example, information on a type of an RF coil, a connection method of the RF coil, and a method of mounting the RF coil on a top board of a bed, information on whether or not there is electrocardiographic synchronization, information on setting of the body position of a tested body and a fixing method thereof, information on whether to use contrast agent or not, information on a type of the contrast agent, and other information necessary for tested body setting) on the past series which is recorded in a shared object.

(Operation)

Next, an operation of the medical image diagnostic system S will be described mainly on the basis of a process performed in the MRI apparatus 5.

First Example

In the first example, a shared object created in a test using an MRI apparatus is used.

Figure 21:
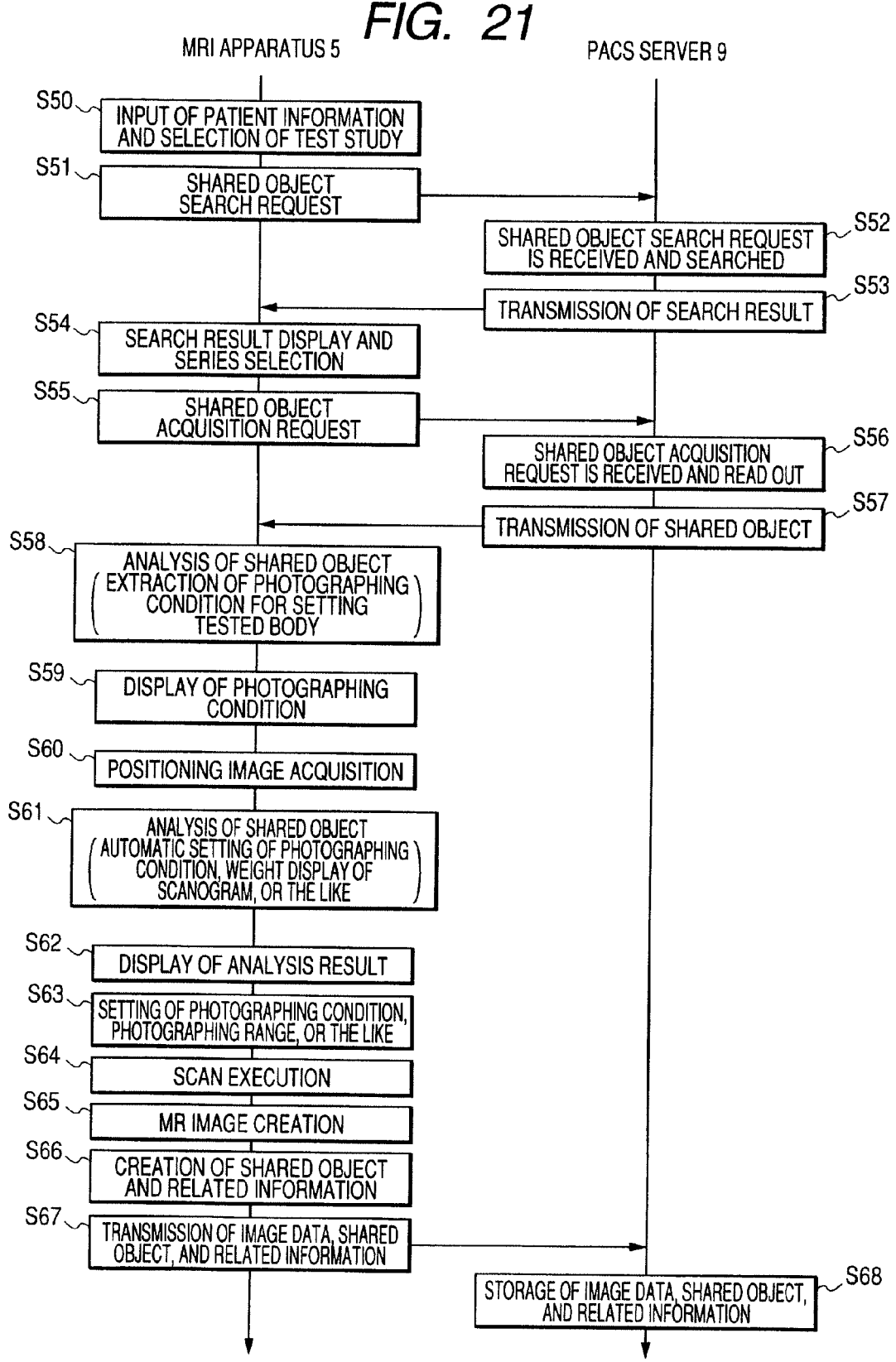
FIG. 21 is a flow chart illustrating a flow of a photographing process performed by the MRI apparatus 5 using a shared object.

FIG. 21 is a flow chart illustrating a flow of a photographing process performed by the MRI apparatus 5 using a shared object. As shown in the drawing, first, when patient information, such as a patient ID, is input to acquire an MR image (step S50), the control unit 502 transmits to the PACS server 9 a search request for past series related to a corresponding patient through the network N (step S51). In response to the search request, the control unit 91 of the PACS server 9 searches a shared object of series related to the patient among shared objects stored in the shared object storage unit 95b (step S52) and transmits a result of the search to the MRI apparatus 5 (step S53). The search result transmitted to the transmitting and receiving unit 508 of the MRI apparatus 5 is displayed on the first display unit 524 in a predetermined form.

Then, when an operator selects desired series from a plurality of series information, which is displayed in the form of a list, through the input unit 131 (step S54), the control unit 502 transmits to the PACS server 9 an acquisition request for a shared object corresponding to the selected series through the network N (step S55). In response to the acquisition request for the shared object, the control unit 91 of the PACS server 9 extracts a shared object corresponding to the series selected from the shared object storage unit 95b (step S56)

and then transmits the extracted shared object to the MRI apparatus 5 through the network (step S57).

The shared object transmitted to the transmitting and receiving unit 508 of the MRI apparatus 5 is analyzed in the shared object analysis unit 506 (step S58), and photographing conditions (for example, information on a type of an RF coil, a connection method of the RF coil, and a method of mounting the RF coil on a top board of a bed, information on whether or not there is electrocardiographic synchronization, information on setting of the body position of a tested body and a fixing method thereof, information on whether to use contrast agent or not, and information on a type of the contrast agent) on the setting of a tested body recorded in the shared object are extracted and displayed on the first display unit 524 and the second display unit 525. A medical technician or the like can easily perform the same tested body setting as in a previous test while viewing a photographing condition displayed on the second display unit 525 within a shielded room, for example.

When the tested body setting is completed, the control unit 202 controls the transmitting unit 518, the receiving unit 519, and the inclined magnetic coil device power 517 according to a photographing condition of a reference image (for example, coronal image acquired by pilot scan) so as to acquire a reference image related to the corresponding tested body and display the acquired image on the first display unit 524 (step S60). The shared object analysis unit 506 analyzes a reference point on the acquired present reference image and a past position determination image included in the shared object and then specifies a reference point on both the images. In addition, the shared object analysis unit 506 analyzes a photographing condition and an image creating condition recorded in the shared object and makes automatic setting such that a condition consistent with present photographing is equal to that of the corresponding shared object.

Figure 22:
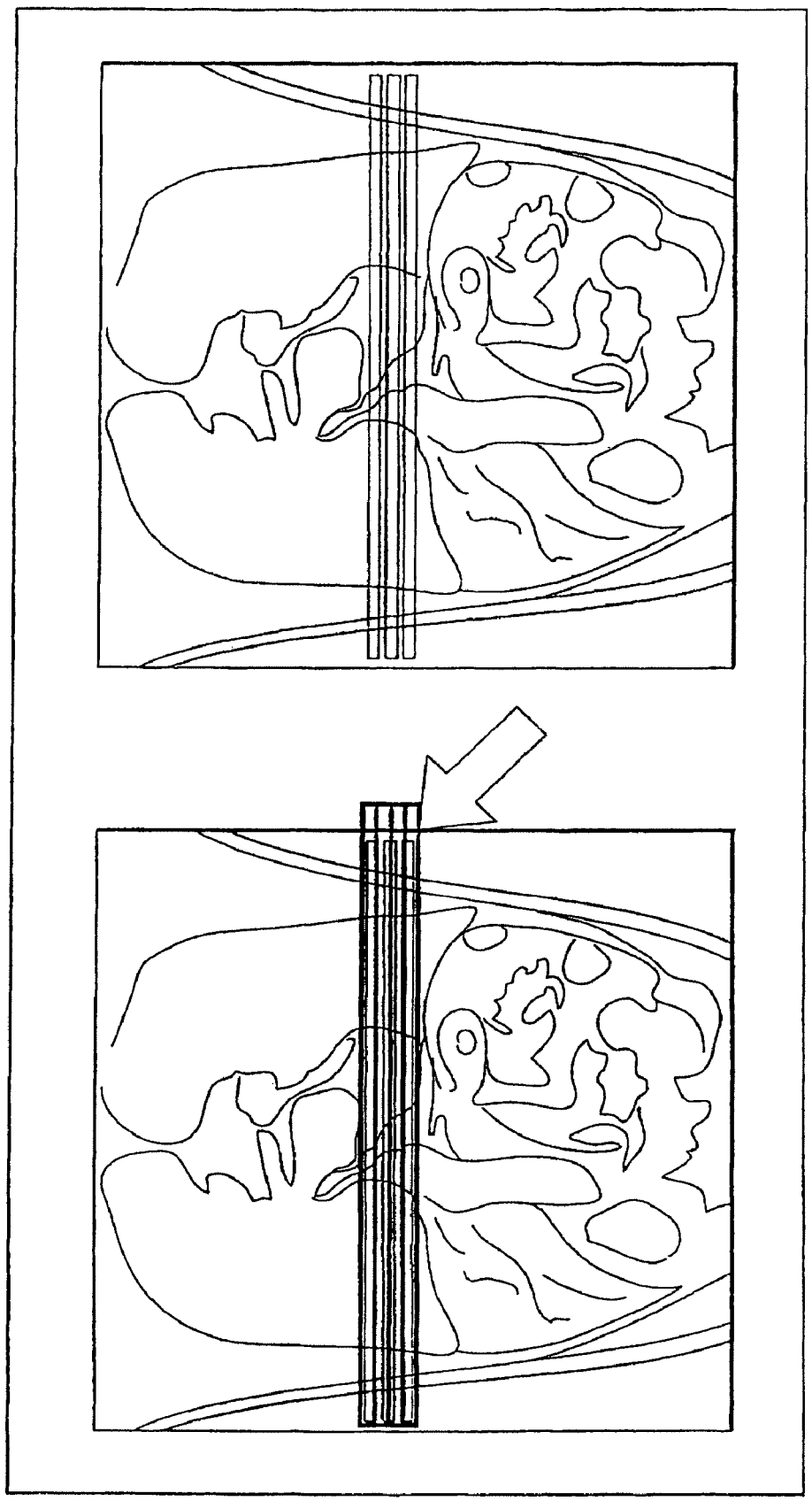
FIG. 22 is a view illustrating an example of a display pattern in which a reference point on a past position determination image included in a shared object and a reference point on a present position determination image correspond to each other.
Figure 23:
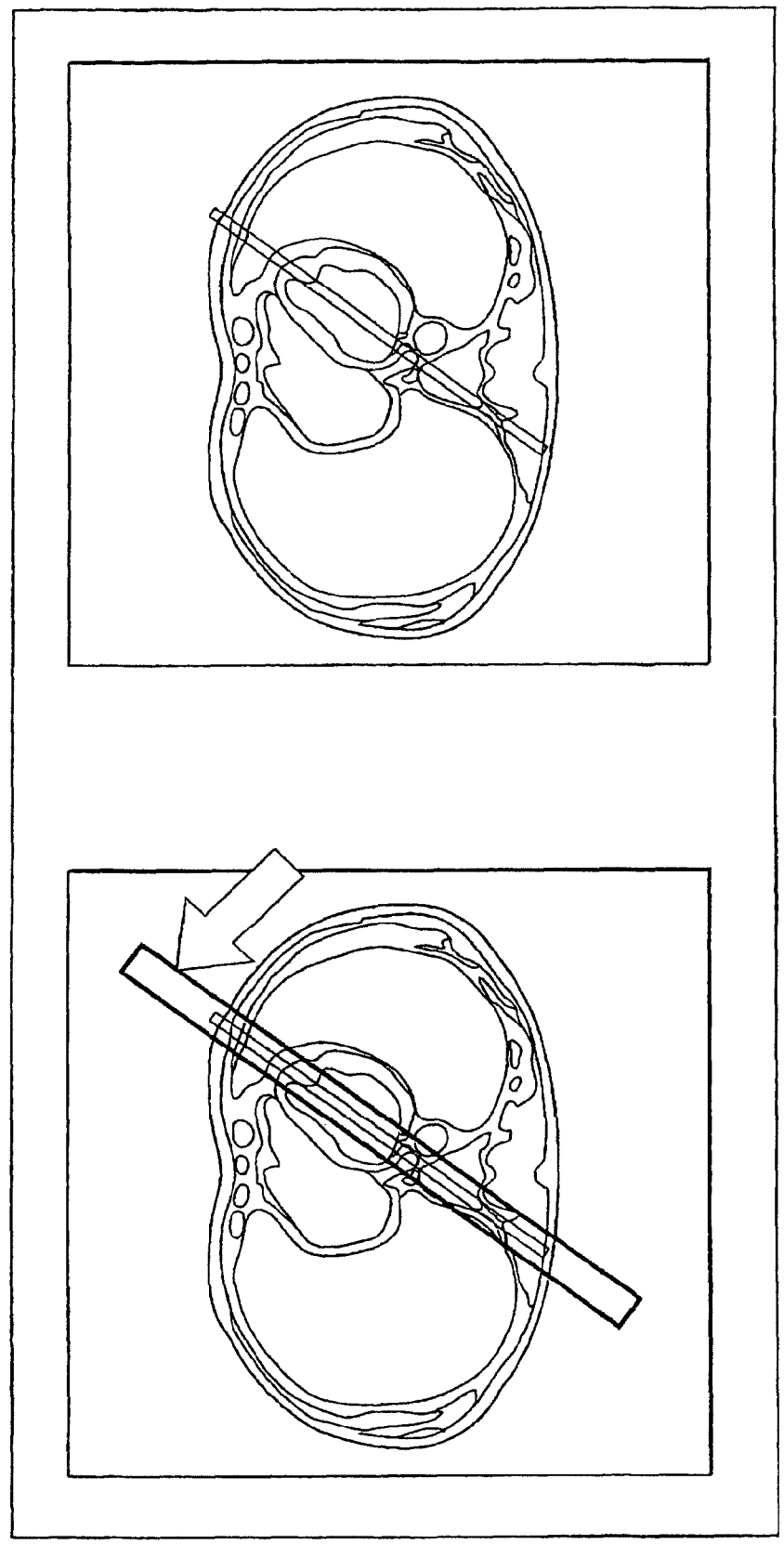
FIG. 23 is a view illustrating an example of a display pattern in which a reference point on a past position determination image included in a shared object and a reference point on a present position determination image correspond to each other.
Figure 24:
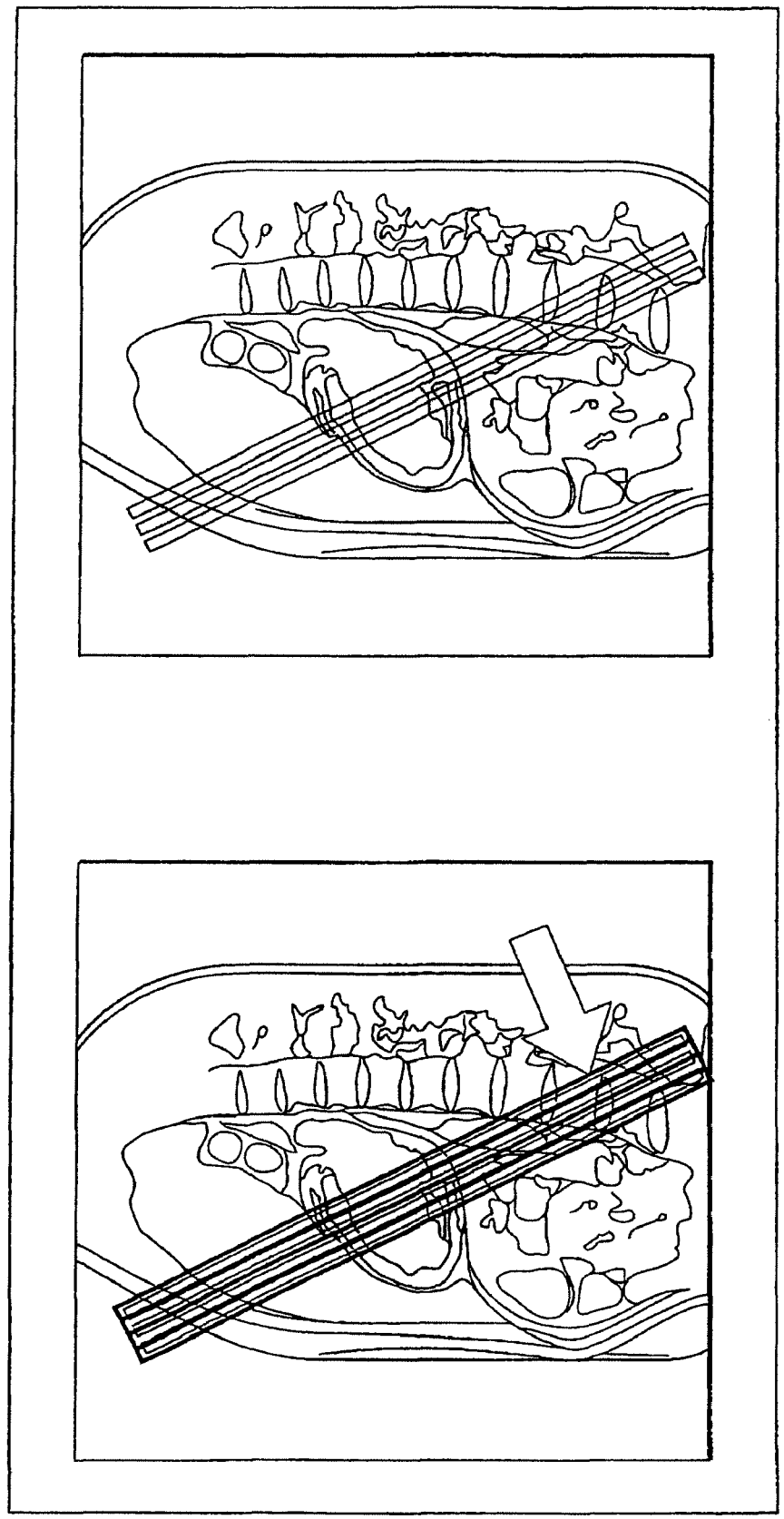
FIG. 24 is a view illustrating an example of a display pattern in which a reference point on a past position determination image included in a shared object and a reference point on a present position determination image correspond to each other.

The control unit 502 displays an analysis result of the shared object on the first display unit 524 in a predetermined form (step S62). Specifically, the control unit 127 displays the analysis result on the first display unit 524, for example, in the form of dialog so that a condition determined to be inconsistent with the present photographing by the shared object analysis can be set and it is possible to determine the availability of the automatically set condition. In addition, the control unit 202 displays both position determination images so as to overlap each other or be adjacent to each other as shown in FIGS. 22 to 24, such that the reference point on the present position determination image and the reference point on the past position determination image included in the shared object correspond to each other.

Then, the control unit 502 sets a photographing range and the other conditions determined to be inconsistent with the present photographing by the shared object analysis on the basis of an instruction of an operator through the operation unit 507 (step S63). When a photographing condition, an image creating condition, and the like are set through the input unit 131, the control unit 502 performs a scan for acquiring an MR image according to the set photographing condition (step S64). The reconstruction unit 504 creates the MR image according to the set image creating condition (step S65). The created MR image is automatically stored in the storage unit 501 as one series information.

Then, the shared object creating unit 505 creates a shared object and creates information related to corresponding series by using information on stored series, a photographing condition used in the corresponding scan, or an image creating condition used in the MR image creation (step S66). At this time, a UID of series select in step S54 is recorded in the shared object as a parent series UID used as a reference of the series.

The created shared object and the relation information are transmitted to the PACS server 9 together with series obtained by the scan, by means of the transmitting and receiving unit 508 (step S67). The PACS server 9 stores the acquired series information in the image storage unit 95a and the shared object and the relation information in the shared object storage unit 95b (step S68).

Second Example

In the second example, a shared object created in a test using an X-ray CT apparatus is used. In addition, a shared object created in a test using an MRI apparatus may be used in a test using an X-ray CT apparatus, without being limited to the above example. In addition, without being limited to the MRI apparatus and the X-ray CT apparatus, the invention may be applied to other cases, for example, a case in which medical image diagnostic apparatuses used in past and present tests are different.

Figure 25:
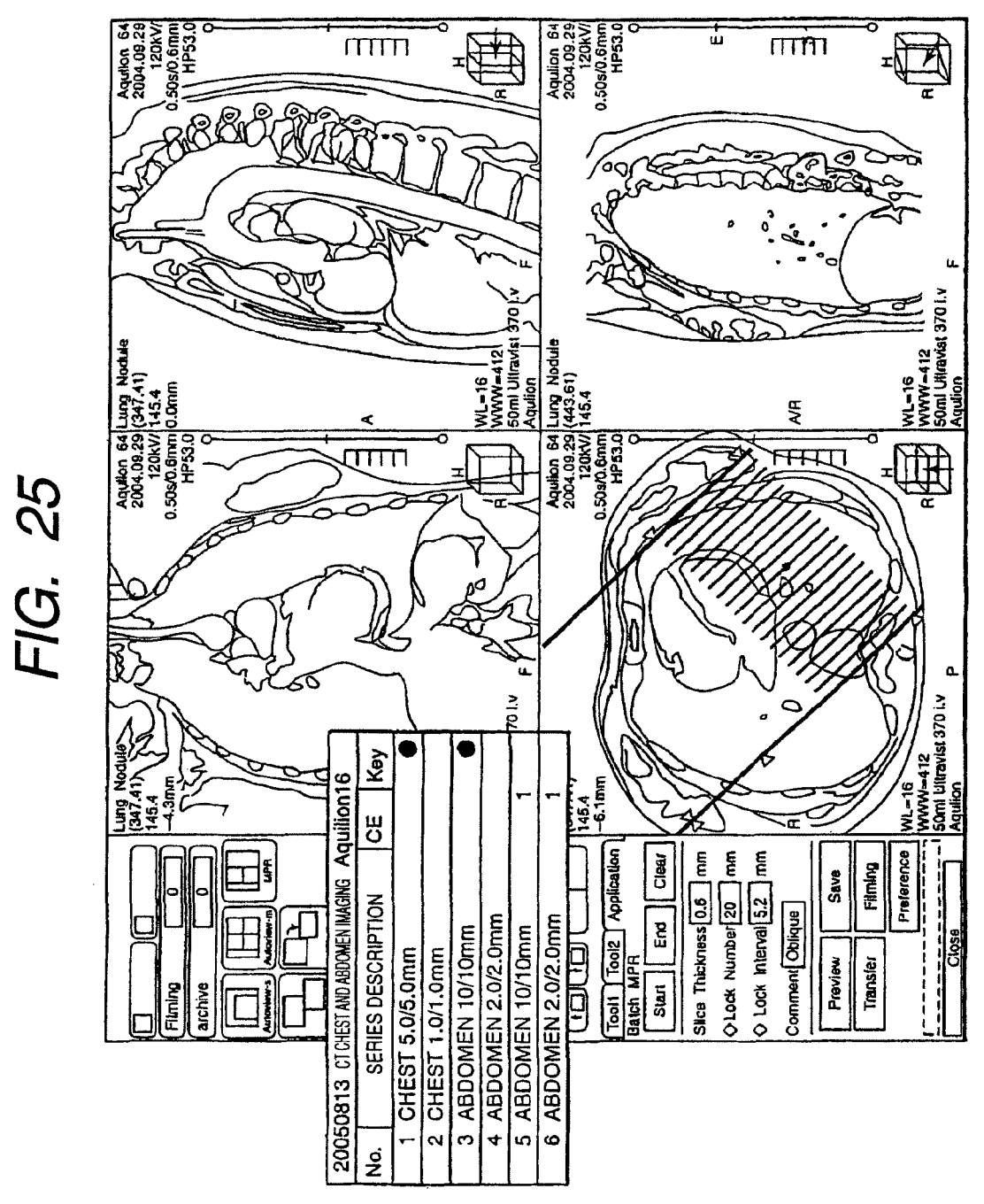

In the present embodiment, in step S54 of FIG. 21, for example, a search result shown in FIG. 25 is displayed. Further, in the shared object analysis in steps S58 and S61, only a condition that can be shared with the MRI apparatus 5 is used. In particular, the position of a scanned cross section and the photographing range (using a position determination image) recorded in a shared object are converted into body coordinates information. Accordingly, even when types of medical image diagnostic apparatuses that are used are different in past and present tests, it is possible to set approximate the same photographing range and position of a scanned cross section. In addition, in the shared object creation in step S66, information on series, a photographing condition used in the corresponding scan, a reference image, an image creating condition used in the MR image creation, and the like are additionally recorded in the shared object to be analyzed in step S 58, thereby creating a new shared object.

According to the configuration described above, the following effects can be obtained.

First, in the medical image diagnostic system, it is possible to automatically set a photographing condition, a photographing range, a tomographic position to be photographed, and an image creating condition, which are the same as those in a past test, by using a shared object having a unified format. Therefore, it is possible to alleviate a labor of a doctor or the like in a photographing step or a report creating step and to reproduce a condition in a past test (for example, previous test) with high precision.

Furthermore, in the medical image diagnostic system, for example, correspondence between a past photographing range and a present photographing range is performed using a body coordinates information recorded in a shared object. Accordingly, even when types of medical image diagnostic apparatuses in past and present tests are different, it is possible to realize high-precision image diagnosis while alleviating the labor of a doctor or the like.

Fourth Embodiment

Next, a fourth embodiment of the present invention will be described. In the present embodiment, it will be described in more detail about an example of an operation of a medical image diagnostic apparatus using a shared object in a step (for example, setting of a patient's bed and acquisition of a position determination image) before the scan. In addition, in the present embodiment, a case in which the MRI apparatus 5 is used as a medical image diagnostic apparatus will be described for the specific explanation. However, the invention is not limited thereto, and it is needless to say that configuration and operation explained in the present embodiment can be applied to the other medical image diagnostic apparatuses.

Figure 26:
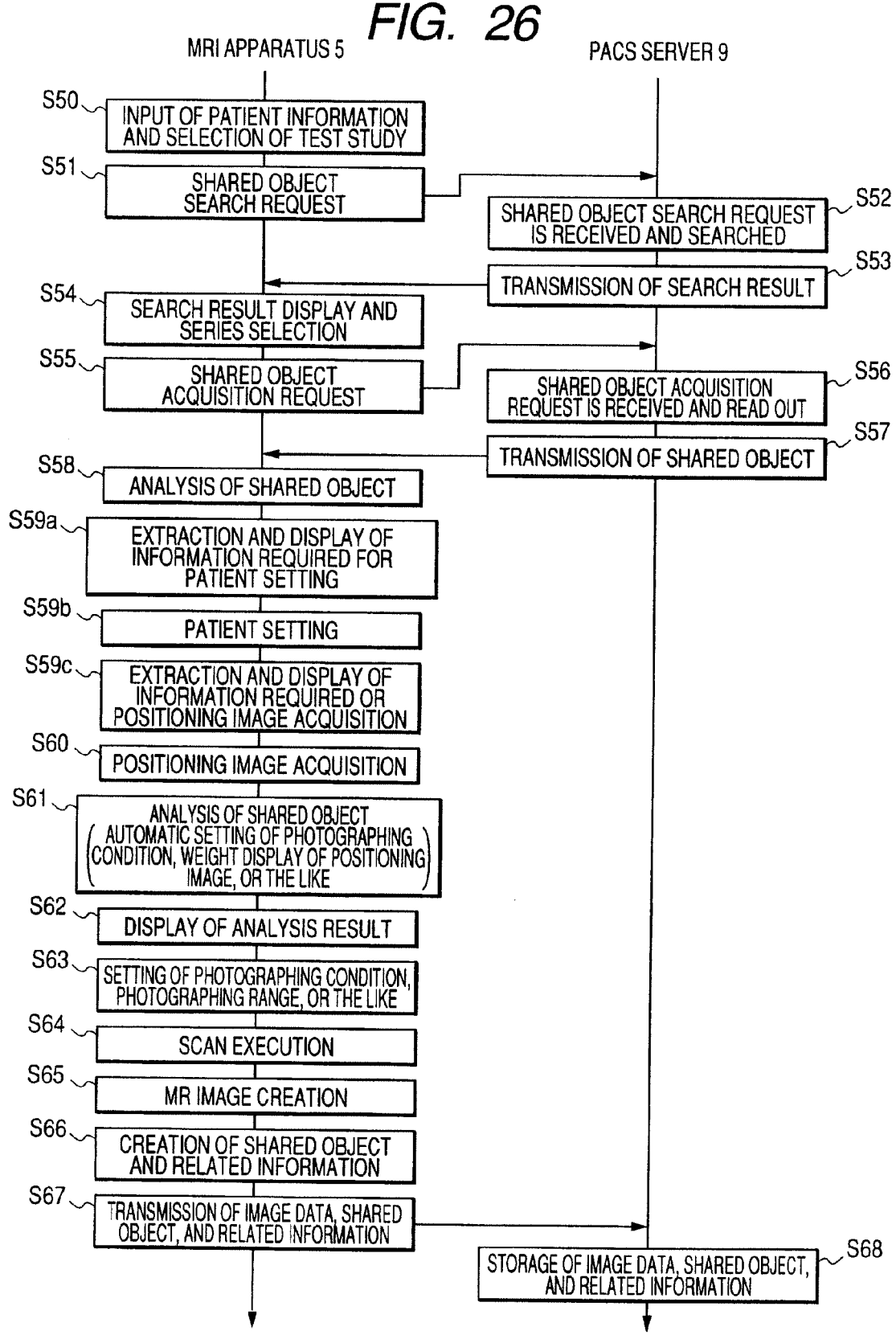
FIG. 26 is a view illustrating a flow (from test request to image test) of a medical act in an image diagnosis according to a fourth embodiment.

FIG. 26 is a view illustrating a flow (from test request to image test) of a medical act in an image diagnosis according to the present embodiment.

As shown in the drawing, first, when patient information, such as a patient ID, is input to acquire an MR image (Step S50), the processes in steps S51 to S58 shown in FIG. 21 are performed. According to a result of the shared object analysis, photographing conditions (for example, information on a type of an RF coil, a connection method of the RF coil, and a method of mounting the RF coil on a top board of a bed, information on whether or not there is electrocardiographic synchronization, information on setting of the body position of a tested body and a fixing method thereof, information on whether to use contrast agent or not, and information on a type of the contrast agent) on the setting of a tested body recorded in the shared object is extracted and is then displayed on the first display unit 524 and the second display unit 525 (step S59a). A medical technician or the like performs setting of a patient to a bed, coil setting, and the like on the basis of a photographing condition displayed on the second display unit 525 within a shielded room, for example (step S59b).

When the setting of a patient to a bed is performed, the shared object analysis unit 506 extracts photographing conditions (for example, a position determination image in a previous test, sound instruction data (for example, information on a sound instruction, such as 'breathe and stop breathing' of a medical technician or the like with respect to a patient performed at the time of photographing a position determination image in a past test; information for determining in which state of inhale and exhale the photographing was performed. Refer to 'previous sound' and 'post sound' in FIG. 15) in a previous test, and information on the position of a key image on the position determination image), which can be used for acquisition of a position determination image, from the acquired shared object. The extracted photographing condition is displayed on the first display unit 524 and the second display unit 525 (step S59c). Further, for example, if the sound instruction data in a previous test is not included as a result of the analysis of the shared object analysis unit 506, it is preferable to display a predetermined message, such as 'no sound instruction data in a previous test'. The medical technician or the like sets a photographing condition for acquiring a position determination image for a present test while referring to the proposed photographing condition.

The control unit 202 controls the transmitting unit 518, the receiving unit 519, and the inclined magnetic coil device power 517 according to the set photographing condition so as to acquire a position determination image related to the corresponding patient and display the acquired image on the first display unit 524 (step S60). Then, the processes in steps S61 to S68 shown in FIG. 21 are performed in the same manner, such that a diagnostic image and a shared object are created for each series.

According to the configuration described above, even in a step before the scan, such as setting of a patient to a bed or acquisition of a position determination image, as well as the scan and a step (for example, a image creating step) after the scan, it is possible to realize efficient or highly reproducible image diagnosis by using a shared object.

Fifth Embodiment

Figures 27, 28:
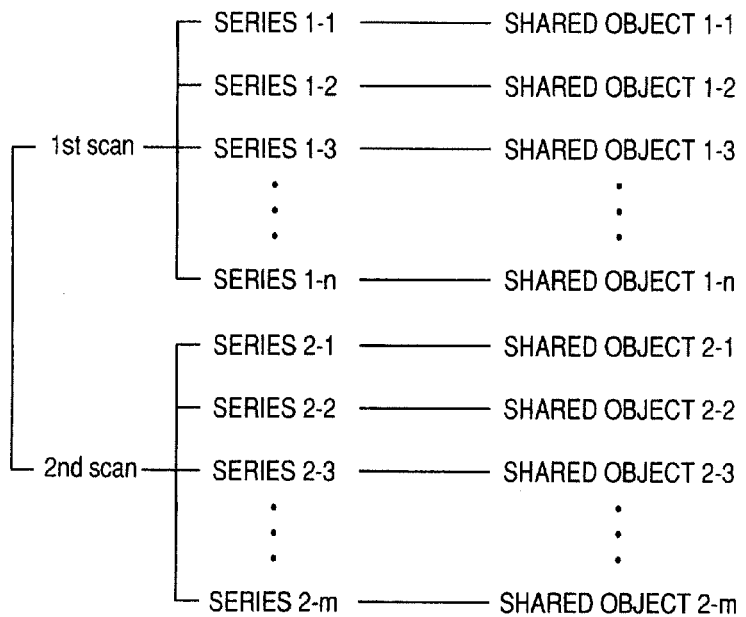
FIG. 27 is a conceptual view explaining diagnosis protocol including a plurality of scan.
FIG. 28 is a view illustrating an example of a search result displayed in step S54 of FIG. 26, for example.
Figure 29:
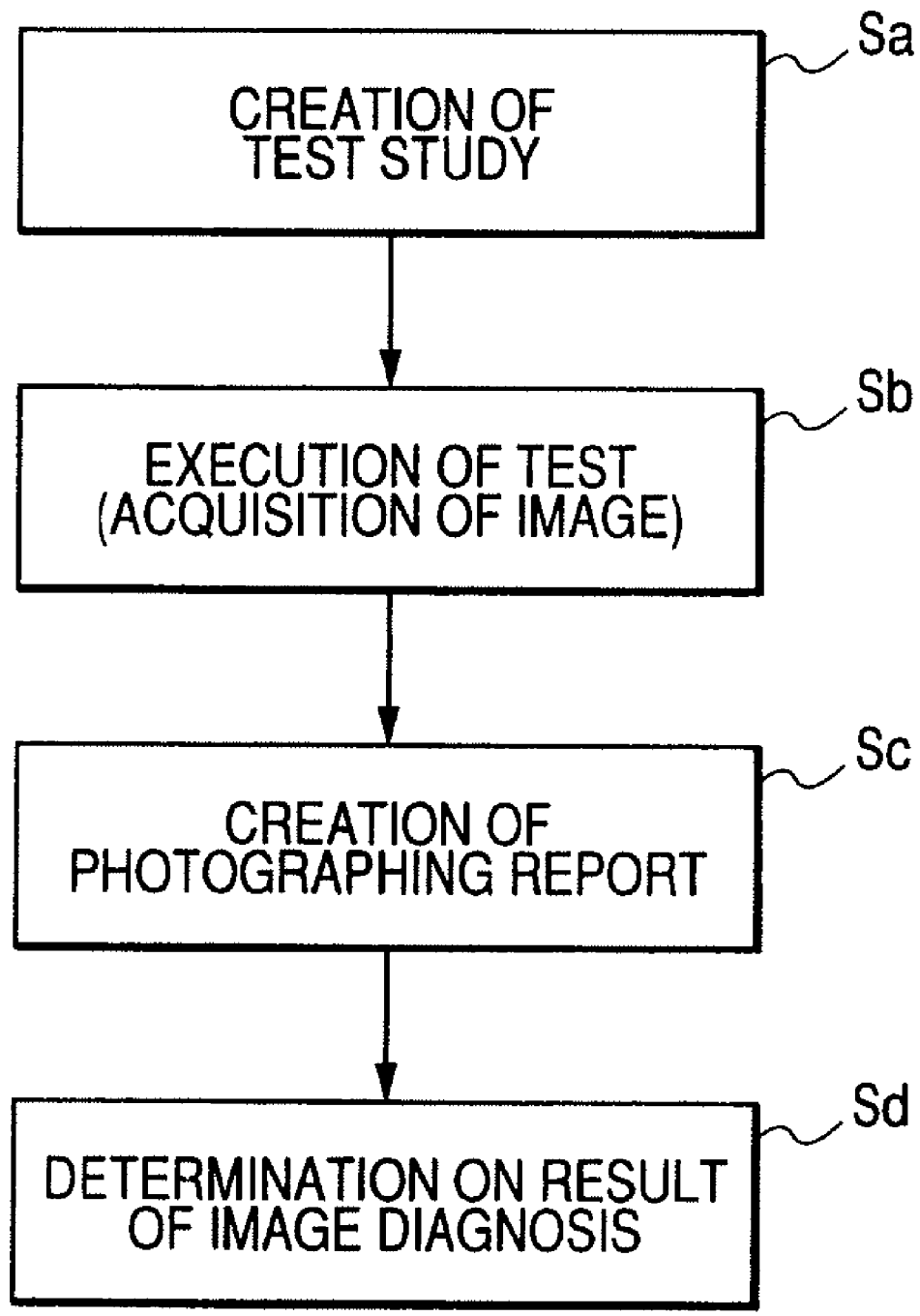
FIG. 29 is a view illustrating an example of a flow (from request from a patient to image test) of a medical act in an image diagnosis.

When a test (study) on a patient is performed, there is a case in which diagnostic protocol including a plurality of scans shown in FIG. 27 is planned and executed. A typical example includes a case in which the chest is photographed by a first scan and the abdomen is photographed by a second scan. In addition, there is a case of creating a plurality of diagnostic images in different image creating conditions by using image data on a predetermined part acquired by one-time scan. A typical example includes a case in which a sagittal image is created as series 1-1 and an axial image is created as series 1-2 by using the image data acquired by the first scan shown in FIG. 27.

On the other hand, a shared object is created for each series. For this reason, in the case of performing the diagnostic protocol shown in FIG. 27, total '(n+m)' shared objects are separately created to be managed.

In the present embodiment, in the case when a plurality of series (and shared objects) are created as a result of one-time scan or one-time execution of diagnostic protocol, an example of efficiently performing a scan plan by the used of a past shared object.

Further, in the present embodiment, a case in which the MRI apparatus 5 is used as a medical image diagnostic apparatus will be described for the specific explanation. However, the invention is not limited thereto, and it is needless to say that configuration and operation explained in the present embodiment can be applied to the other medical image diagnostic apparatuses.

FIG. 28 illustrates an example of a search result displayed in step S54 of FIG. 26. In the drawing, series 1-1 to series 1-n are based on the first scan (for example, chest scan) and only image creating conditions thereof are different from one another. In addition, series 2-1 to series 2-n are based on the second scan (for example, abdomen scan) and similarly, only image creating conditions thereof are different from one another.

As an operation in step S55 of FIG. 26, it is assumed that an acquisition request for shared objects corresponding to, for example, the series 1-1 and 1-2 among the plurality of series displayed as the search result as shown in FIG. 28 is made. In the case, the shared object analysis unit 506 analyzes a shared object 1-1 corresponding to the series 1-1 and a shared object 1-2 corresponding to the series 1-2 and makes a variety of determination on whether or not photographing conditions on setting of a patient, position determination images, photographing conditions on position determination images, photographing conditions on the scan, image creating conditions, and the like are repeated. For example, the shared object analysis unit 506 determines that the shared object 1-1 and the shared object 1-2 have the same position determination images, photographing conditions on position determination images, and photographing conditions on the scan but have different image creating conditions.

Accordingly, in steps S59a, S59c, and S63 shown in FIG. 26, a photographing condition or a position determination image common to the shared object 1-1 and the shared object 1-2 are used. For this reason, even if two kinds of shared objects are used in the present photographing, it is possible to complete setting a photographing condition in acquiring a position determination image at a time. On the other hand, since the image creating conditions of the shared objects 1-1 and 1-2 are different, in the step S65, two kinds of images of an MR image conforming to the image creating condition included in the shared object 1-1 and an MR image conforming to the image creating condition included in the shared object 1-2 are automatically created.

Furthermore, for example, in the case when the series 1-1, 1-2, 2-1, and 2-2 are selected among the plurality of series displayed as the search result as shown in FIG. 28, a first scan for the chest intended to reproduce the series 1-1 and 1-2 and a second scan for the abdomen intended to reproduce the series 2-1 and 2-2 are automatically planned. The processes in steps S58 to S68 are repeated on the basis of the shared objects 1-1 and 1-2 in the first scan and on the basis of the shared objects 2-1 and 2-2 in the second scan.

According to the configuration described above, even in the case when a plurality of shared objects corresponding to a plurality of series are used, it is possible to make an efficient scan plan by determining information repeated among the shared objects and other information. As a result, since input of a variety of conditions that are required is reduced to the requisite minimum, it is possible to alleviate a labor of a medical technician or the like and to realize acquisition of an image having high reproducibility.

In addition, the present invention is not limited to the above embodiments and various modifications may be made without departing from the spirit and scope of the invention. Specific modifications are as follows, for example.

Each function according to each of the embodiments may be realized by installing a program, which executes a corresponding process, in a computer, such as workstation, and loading the program into a memory. At this time, it is possible to store a program, which allows a computer to execute a corresponding method, in a recording medium, such as a magnetic disc (for example, floppy (registered trademark) disc or hard disc) or an optical disc (for example, CD-ROM or DVD), or a semiconductor memory so as to be distributed.

In addition, a variety of inventions may be realized by proper combination of the plurality of constituent elements disclosed in the above embodiments. For example, several constituent elements may be omitted from the entire constituent elements explained in the above embodiments. Moreover, the constituent elements in different embodiments may be properly combined.

According to the invention, it is possible to realize a medical image diagnostic apparatus, a picture archiving communication system server, an image reference apparatus, and a medical image diagnostic system that are capable of creating shared information, by which medical information in the past can be widely applied and be reproduced with high precision, and of efficiently utilizing the shared information.

What is claimed is:

1. A medical image diagnostic apparatus, comprising:
   an input unit configured to input a scan condition and scan position information by using a position determination image of a tested body;
   a data acquisition unit configured to acquire data for creating an image of the tested body based on the scan condition and the scan position information;
   an image creating unit configured to create a first image based on the acquired data;
   a file creating unit configured to create a file to be shared in which the scan condition and the scan position information are added to the position determination image;
   a relation information creating unit configured to create relation information between the file to be shared and the first image; and
   a storage unit that stores the file to be shared and the relation information in association with each other.

2. The medical image diagnostic apparatus according to claim 1,
   wherein the file creating unit is configured to create body reference coordinates indicating a position of at least one of a reference point on the position determination image and a photographing range with a body structure as a reference, and to include the created body reference coordinates in the file.

3. The medical image diagnostic apparatus according to claim 1, further comprising:
   a designation unit that designates, as a key image, at least one of a plurality of images created by the image creating unit; and
   a display unit that displays a mark indicating a position of the key image together with the position determination image.

4. The medical image diagnostic apparatus according to claim 3, further comprising:
   a report creating device configured to create a report based on the key image.

5. The medical image diagnostic apparatus of claim 3, wherein the file creating unit is configured to create the file to be shared so that the file includes a file identifier, a parent file identifier identifying a parent file referred to when creating the file, and a relation series identifier identifying a series that uses a same scan condition or a same scan position information as that used for the first image.

6. The medical image diagnostic apparatus according to claim 1,
   wherein the file further includes unique file information having at least one of a first identifier serving as information for distinguishing the file from other files, a second identifier serving as information for specifying another file referred to in creating the file, and a third identifier serving as information specifying an image acquisition process related to an image acquisition process whose characteristic is indicated by the file.

7. The medical image diagnostic apparatus according to claim 6,
   wherein data specified by the identifier included in the unique file information and the file are linked to each other.

8. The medical image diagnostic apparatus according to claim 1,
   wherein the medical image diagnostic apparatus is an X-ray computerized tomography apparatus;
   the file includes a photographing condition that includes at least one of a bed movement amount in an image acquisition process, a tube current or a tube voltage of an X-ray tube which is an illumination unit, a bed movement amount in one rotation corresponding to an image width of an obtained tomographic image, an insertion direction of the tested body in a test, a body position of the tested body in a test, information on whether to use a contrast agent or not, an amount of the contrast agent to be used, and a type of contrast agent; and
   the file includes an image creating condition that includes at least one of a reconstruction range, time phase of the plurality of images, a position of each of the plurality of images, directions of the plurality of images, a thickness of each of the plurality of images, a magnification rate, and a reconstruction function.

9. The medical image diagnostic apparatus according to claim 1,
   wherein the medical image diagnostic apparatus is a magnetic resonance imaging apparatus,
   the file includes a photographing condition that includes at least one of an insertion direction of a tested body in a test, a body position of a tested body in a test, a magnetic field intensity, a used pulse sequence, a type of detection coil, a location where the detection coil is provided, information on whether or not there is electrocardiographic synchronization, information on whether or not there is breathing synchronization, information on whether or not there is ventilation for a bed, and a body portion serving as a photographing reference, and the file includes an image creating condition that includes at least one of a reconstruction range, time phase of the plurality of images, a position of each of the plurality of images, directions of the plurality of images, a thickness of each of the plurality of images, a magnification rate, and a reconstruction function.

10. The medical image diagnostic apparatus of claim 1, wherein the relation information creating unit is configured to create the relation information, the relation information including a correspondence table between a file identifier of the file and a series identifier of a corresponding series.

11. The medical image diagnostic apparatus of claim 1, further comprising:

a transmitting unit configured to transmit the first image, the file, and the relation information to a server.

* * * * *